(12) United States Patent
Kang et al.

(10) Patent No.: US 8,771,936 B2
(45) Date of Patent: *Jul. 8, 2014

(54) BACTERIOPHAGE AND ANTIBACTERIAL COMPOSITION COMPRISING THE SAME

(71) Applicant: CJ Cheiljedang Corporation, Seoul (KR)

(72) Inventors: In Hye Kang, Suwon-si (KR); Min Tae Park, Seoul (KR); Young Wook Cho, Seoul (KR); Soo An Shin, Seoul (KR); Hyang Choi, Anyang-si (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/621,730

(22) Filed: Sep. 17, 2012

(65) Prior Publication Data

US 2013/0022579 A1 Jan. 24, 2013

Related U.S. Application Data

(63) Continuation-in-part of application No. 12/560,263, filed on Sep. 15, 2009, now Pat. No. 8,288,146.

(30) Foreign Application Priority Data

Dec. 24, 2008 (KR) .................. 10-2008-0133909

(51) Int. Cl.
*C12Q 1/70* (2006.01)
*A61K 39/112* (2006.01)

(52) U.S. Cl.
USPC ............................................ 435/5; 424/93.6

(58) Field of Classification Search
None
See application file for complete search history.

(56) References Cited

U.S. PATENT DOCUMENTS

| 6,485,902 | B2 | 11/2002 | Waddell et al. |
| 6,942,858 | B1 | 9/2005 | Ghanbari et al. |
| 8,288,146 | B2 * | 10/2012 | Kang et al. ............. 435/235.1 |
| 2004/0208853 | A1 | 10/2004 | Sulakvelidze et al. |

OTHER PUBLICATIONS

O'Flynn, et al. Journal of Applied Microbiology, 2006, 101:251-259.
Barrangou, et al. Applied and Environmental Microbiology, 2002, 68(11):5452-5458.
Goto, et al. J. Food Hyg. Soc. Japan, 2004, 45(1):25-28.

* cited by examiner

*Primary Examiner* — Bao Li
(74) *Attorney, Agent, or Firm* — Seed IP Law Group PLLC

(57) ABSTRACT

The present invention relates to a novel bacteriophage, more particularly, a bacteriophage that has a specific bactericidal activity against *Salmonella typhimurium, Salmonella gallinarum*, or *Salmonella pullorum*, a composition for the prevention or treatment of infectious diseases including salmonellosis and *Salmonella* food poisoning caused by *Salmonella typhimurium*, Fowl typhoid caused by *Salmonella gallinarum*, and Pullorum disease caused by *Salmonella pullorum*, which comprises the bacteriophage as an active ingredient, and an animal feed, drinking water, cleaner, and sanitizer which comprise the bacteriophage as an active ingredient. The present invention also provides important insights into prevention and control strategies against *Salmonella* infection and suggests that the use of bacteriophage can be a novel, safe, and effectively plausible alternative to antibiotics for the prevention of *Salmonella* infection in poultry.

2 Claims, 5 Drawing Sheets

SEQUENCE LISTING

<160> NUMBER OF SEQ ID NOS: 9

<210> SEQ ID NO 1
<211> LENGTH: 3083
<212> TYPE: DNA
<213> ORGANISM: Bacteriophage KCCM 10976P

<400> SEQUENCE: 1

```
tggataactt ctggcagcgc caggcacagc gtcgtctgat tgctaccgct ctcggcctgt      60
acaacgataa cgttgctgca accgacgaat accacaccca gaacgacatg gttatcgatg     120
tatccgccac catgggcttt gatgcgggtg cctttatcga cgccaccag actatgggcg      180 acgcgctgat gggctcaact ggtgaagtgc tcggtgctat tgcgatgcac agcttcgtgt     240
acggccaggc acgtaaagcc aacctgattg acttcatccg tgactccgaa aataacacca     300
tgtttgctac atatcagggc taccgcgtgg ttgttgatga tagcatgacc gttgtaggca     360
ccggtaatga ccgcaagttt atcagcatca ttttcggcaa cggcgcaatc ggctacggcg     420
aaggtactcc ggagaaccca ctggaatatg agcgtgaagc ctcacgcggt aacggcggcg     480
gtgttgaaac cctgtggacc cgtaaaacct ggctgctgca cccgctgggc tacagcttca     540
ctagcgcggt aatcaccggt aacggctccg aaaccatcgc ccgctccgct tcctggcagg     600
acctggcgaa cgccgccaac tggaatcgcg tagtagagcg caaacacgtt ccaatcgcgt     660
tcctggttac tggcgtaggc gcgtaacagt agcgtataat caggaggggc tacggcccct     720
cttttcacat tcatacggga gaaatgtatg gcaccacag gtaaagggct gccacgcagt     780
ctgaaagacg ccaaactgaa catccctatg gcgactacat cggatgttgg tggcgtaaaa     840
aagtcagcta ctgtagcctc gccagccgct attactgctg ccgcaggaac ccaatcagtc     900
gccgacccta ctaaggccga atttgatgca ctcgtggcgg agtacaacaa actccgaacc     960
gatgtcacag cgctgcgcac taccgtagca aacctgttaa ccgcgcttaa aaacgctgga    1020
actgtaagct aaaggagctt aaaaatggtt gatgtaatta aacgccgtat ggtaggcgtc    1080
tccgacgact cccctgctga tggtcaggta gaaatcgaca tggtaaacat ttccccagcg    1140
tcgttttcta caggcctgaa tgacactacg gcagtaaccg caccggcggc gctgacactc    1200
accgtagcgg cggcagggg ccgagagcca tacagctatc agtggttcaa aaacggtaac    1260
gccatttctg gcgcaacggc ggcgacttac actaagacgc ctaccgttgc cacggttgat    1320
tccggcactt acaaagttgt tgcccaggat ggttatggta atatcatctc agacagcact    1380
attgtcacag tatcttaatt aaacggccct tcggggccgt catagggaaa cataatggtt    1440
aatgacaatt acgtaatccg cgagaaatat aacggtctgg tagagattga cggccagctc    1500
gtaccacagc gcggaaatgt tctgccggaa gaactggtgg caacgcaacc ggataacgaa    1560
gaagcgcaca ataacggtgg cggcgccgag cctaaacgcc gtcgtcgtcg cacgttcgag    1620
gaataaccaa tggctttagt cgtcgaagat ggttctatag ttgcaggagc tgacagctat    1680
cttagcctgg aggacgcccg cgcactggcg gctaaatacg gctatgtgtt acccgctgag    1740
ggtaatgagg ctgaagccgc gctccgcaat ggtgcgatgt acgtcggttt acaagagcct    1800
gctatgtgtg gtcgtcgtgt atccgcgacg cagtccttat cgtttccgcg cactggaatt    1860
agtctgtacg gtttccctgt ggcgagtaat gttatcccgg accaggttaa actcgcgcag    1920
cttatcgctg gcgtagagta cggtaacggt gcggatgtgc gcgccagttc agacgggcgt    1980
gttacgacta tggagcgcgt agaaggtgcg gtgacagtac agtacgccaa caacggcaac    2040
accgggtcga caatcactat cacggcatct atggacgcat tacgcccgct gctgtgtggc    2100
```

```
tccaacaacg ctttctcttt taatgtttat cggggttaga gatggctaaa acgaagagtg    2160
aaatgtttgc gcttatcggg ggcaattttc cggataacac gaccggagcc atcacaccag    2220
aaaagctaag agaagtaaca acgcaactgg cagactctat gttgtatgct gccactggag    2280
tgaaagaggt ggaagtactg agggcctctt ctactgtcgc acaagcacca acggcagttg    2340
acactgcgtt acagttatct tttggcgcag ctcagggcgc ggcatctaac ccagttatga    2400
ttaacgcggc cggtcttgtt acgtttaaca ccgcgggtaa ttatgcggtt cgcatcaaat    2460
tacaggcggg gcgcacaggg gccagtggga cttctattct gttatcgcgc attcttgtga    2520
acgggtctca atacggttca cctgcggcta ccaagctagt aagcgcggac gttacgatac    2580
ctatagaatc ccgcgtcgtt attaacgctg ccgcagggca gactatggct gtgcagatta    2640
tgagagatag cgcaggcact aattttggcg gtgtatatcc gcagactgcg accgtagctg    2700 cgtgggcat cgctccgtct gcgttactcg tcatctcaag actggagccc gcctaatgag    2760
cactgctttc agcaagaaaa tgcagggcgt ggagacacgc ctgttaggca aatatggcag    2820
cactgtaacg ctggttcgcg ctggttctaa ggtctgggac gaaagccttg gcgaatacgt    2880
gcgacagcca gatactcaga ttcctcttac cgccgtcccg gtgccgatta acgcggggct    2940
tgtcaacgga actaccattc aggtggggga tatggtggtg aaagcggact atagtgtgct    3000
gccgaagatg gaagataagg tagaattttc tggggagcaa tggtcagttg tcggtatcga    3060
gaagaaaatc gttaacgatg ata                                           3083

<210> SEQ ID NO 2
<211> LENGTH: 1670
<212> TYPE: DNA
<213> ORGANISM: Bacteriophage KCCM 10976P

<400> SEQUENCE: 2
atcgggatac cccgatgaac ttcgttgtca ataatatacc ggatggagtg ccggtgcgtg      60
tctttatcga tgagataggc gaagacaacg atgttactga ggatttcgaa gcattgaaag     120
aagacgcaat ctttcatgtt gttgagtccg cgggtggcgg agctattaaa ggtgtcatga     180
agattttcag tgtagtttta aaaccactgg cgaagctttt gtccccttca gtaaaaggtg     240
cgtcgtcaaa cctcgctaac tcgcaagcag actcccccaa caacagtctt tctgaccgca     300
ataataaagc gcgtccctat gagcgtagct atgcacatttg cggacggtg caaacgatac     360 caaacaacct tatgtcaact tataaggtgt ttaacgcagc gggtcgcatt atagaatatg     420 gatactcacga tgctggtaga ggttatcttg acatacaccc tgacgaaata acagacggtg     480
atacccgtgt atctgacatc acagggacat cagttgccgt ctacgcgccg tacacgtcac     540
cgaataacac ggcaacgccg caagtactgg ttggagaccc gatagagcag gggttatatc     600
tgactgtcga atcaaatgaa gtagacggcg tggttctgaa agcacaaaac ggacttggca     660
tctcgttttc ttacatgtcc ggatacccct cgttatccgg ttccaccggc actatatacg     720
acccgtcagg ggggtctgac ttctccggtg ttcttgtgcc gaatgatacg ttttctctcg     780
tatccgcctg gacaaataca gatgttgacc tttccggtgg tggttatcag gtaataagtg     840
tttccgaagg aactgttact ttcgtagtcc ccggtaatct tataagtaaa tggcaacaaa     900
tacagccggg ttcgtttttt cgtggagacg gcgaagcctc gttgcaaccg ataacacat     960 atgaaaaac gttaactgat tgggtgtcca taaaccgaac tgaggtggaa cgtattgtcg    1020
ctaacatagc ggccgcaaac gggatgtata agacaatgg tcgttccaaa acgttggctt    1080
```

| | |
|---|---|
| cggtaacagc agaaatacaa taccaacttc ttgacgaaaa tagcgtgccc tacgcccga | 1140 |
| tttacgcggc gcaaggaacc gtatccgggc gcacttctga ctataacggc gtgactatat | 1200 |
| acgcagattt acccgtagcg tctcgtgttc gcgtcagggc gaggagagta acagaccttg | 1260 |
| atttcaattt cgaaggctca gttgtcgacg aaataaccta cgttaacctg tacgggcaga | 1320 |
| ctagagacaa caccccacac tacggcaacc gaaccactgt gcactcaatg cgtaagcaga | 1380 |
| cgccgcgcgc tgccgaagtt aagcaacctc agttgcgcat gattgcgacc gagatggtat | 1440 |
| ataaatatct tgggaatgga gtgtttgagg atacgatgtc gcctaataac caggcagtcc | 1500 |
| aatcgttaat tcgcctcgca agggaccctg acgtcggcgg gctcgattta acagtaagga | 1560 |
| atatggataa gttgcttgct gtacaaaagg aaatagagga ttacttcggc gacaagcaag | 1620 |
| ccggagaatt ctgttacacc ttcgatgatt ataaaacaac gatgcaggat | 1670 |

<210> SEQ ID NO 3
<211> LENGTH: 790
<212> TYPE: DNA
<213> ORGANISM: Bacteriophage KCCM 10976P

<400> SEQUENCE: 3

| | |
|---|---|
| atcgaggcca gcttcgaagg tcgcaagagc cgtcttttca ccagccagcc atgcaagacc | 60 |
| gcgcccttcc acgttggaat aatcggcaac cagtagctta ttaccgggtg taggcaccac | 120 |
| gcagctacga acagttgtgg ctgttaattt cgatacgtca taggcccagt gcgctcgacc | 180 |
| ttttagcagc atgtcaatgc cagttgatag cgcgtgctta cgcaacaggt aattacgctc | 240 |
| agactcaccg ggcatccgaa ttactttatc ctccgggtca tcatcgtaat agccacgagc | 300 |
| taagttctga ggctggaagc ctttacccgc aaaacgtaaa gtcctggacg ctccgccgta | 360 |
| ctggagacaa ccacgacgac gaccgtcggc ggacagacca agcaggagcg ggttgtactt | 420 |
| ggtcgatgcc gtggagctgg cccccagacg catttcgata agtgtacgag cgtcgtcagg | 480 |
| caggtcatcg tcagccagca agtcgtttag cgtggacttc tgcgcgttga gaatctcatg | 540 |
| acctggtgcg aggtctcgca gcgtaggcag aaaatcagca ccggtaagac ccgcgcccca | 600 |
| tttggcgttt gcttcagcct gtagttcaat cttgtgctgc ttcaccgcgt cgattgccgc | 660 |
| attagccagc gccgtgtcga cgtagaagcc gcggtcgttg atgcgctggt cgacagccag | 720 |
| gacggtgttc tcgaactcgg tgttgcccca ctgcggcagc gagtgataaa cctcgcgcat | 780 |
| agatgtgata | 790 |

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4

| | |
|---|---|
| aagacttcgc attataataa gtg | 23 |

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5

| | |
|---|---|
| ttaaagtttg taactcgtac ac | 22 |

```
<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
ccgaaactcc catgaataaa t                                          21

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ttatagttct catcgtcgag                                            20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
cgcataactg ggttgcagga                                            20

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
gagagtactg tgttgctatt ta                                         22
```

BACTERIOPHAGE AND ANTIBACTERIAL COMPOSITION COMPRISING THE SAME

CROSS-REFERENCE TO RELATED APPLICATIONS

The present application is a continuation-in-part of and claims priority to co-pending U.S. patent application Ser. No. 12/560,263, entitled "Novel Bacteriophage and Antibacterial Composition Comprising the Same," filed in the U.S. Patent and Trademark Office on Sep. 15, 2009 and having a common inventor as the present document which claims priority to KR 10-2008-0133909, filed Dec. 24, 2008. The above-referenced applications are incorporated herein by reference.

TECHNICAL FIELD

The present invention relates to a novel bacteriophage, a composition comprising the bacteriophage, and a method for preventing infectious diseases caused by *Salmonella* using the bacteriophage.

BACKGROUND ART

*Salmonella* is a genus of the family Enterobacteriaceae, characterized as Gram-negative, facultatively anaerobic, non spore-forming, rod-shaped bacteria, and most strains are motile by flagella. *Salmonella* has an average genome GC content of 50-52%, which is similar to those of *Escherichia coli* and *Shigella*. The genus *Salmonella* is a pathogenic microorganism that causes infections in livestock as well as in human. *Salmonella enterica*, a species of *Salmonella* bacterium, has a variety of serovars including *Gallinarum, Pullorum, Typhimurium, Enteritidis, Typhi, Choleraesuis*, and derby (Bopp C A, Brenner F W, Wells J G, Strokebine N A. *Escherichia, Shigella, Salmonella*. In Murry P R, Baron E J, et al., eds Manual of clinical Microbiology. 7th ed., Washington D.C. American Society for Microbiology 1999; 467-74; Ryan K J. Ray C G (editors), 2004, Sherris Medical Microbiology (4th ed). McGraw Hill. ISBN 0-8385-8529-9). Of them, *Salmonella Gallinarum* and *Pullorum* are fowl-adapted pathogens, *Salmonella Typhi* is a human-adapted pathogen, *Salmonella Choleraesuis* and derby are swine-adapted pathogens, and *Salmonella* Enteritis and Typhimurium are pathogenic for both human and animals. Each serovar causes illness in that species, resulting in serious negative effects for farmers or consumers.

A disease of domestic birds caused by *Salmonella* bacterium is Fowl Typhoid (FT), which is caused by a pathogen, *Salmonella Gallinarum* (hereinbelow, designated as SG). Fowl Typhoid (FT) is a septicemic disease of domestic birds such as chicken and turkey, and the course may be acute or chronic with high mortality. Recently, it has been reported that Fowl Typhoid frequently occurs in Europe, South America, Africa, and South-East Asia, and damages are increasing. Outbreaks of FT in Korea have been reported since 1992 and economic losses from FT in brown, egg-laying chickens are very serious (Kwon Yong-Kook. 2000 annual report on avian diseases. Information publication by National Veterinary Research & Quarantine Service. March, 2001; Kim Ae-Ran et al., The prevalence of *pullorum* disease-fowl typhoid in grandparent stock and parent stock in Korea, 2003, Korean J Vet Res, 2006, 46(4): 347-353).

Pullorum disease is also caused by one of *Salmonella* bacteria, *Salmonella Pullorum* (hereinbelow, designated as SP). Pullorum disease occurs in any age or season, but young chickens are particularly susceptible to the disease. During the past century, Pullorum disease as an egg-transmitted infection has seriously affected young chickens at 1-2 weeks of age or younger in the world and Korea. In the 1980's, disease occurrence greatly decreased. However, incidence began increasing in the mid 1990's (Kwon Yong-Kook. 2000 annual report on avian diseases. Information publication by National Veterinary Research & Quarantine Service. March, 2001; Kim Ae-Ran et al., The prevalence of *pullorum* disease-fowl typhoid in grandparent stock and parent stock in Korea, 2003, Korean J Vet Res, 2006, 46(4): 347-353).

In Korea, outbreaks of Fowl Typhoid and Pullorum disease have been increasing since the 1990's, inflicting economic damages on farmers. For this reason, a live attenuated SG vaccine has been used in broilers for the prevention of Fowl Typhoid from 2004 (Kim Ae-Ran et al., The prevalence of *pullorum* disease-fowl typhoid in grandparent stock and parent stock in Korea, 2003, Korean J Vet Res, 2006, 46(4): 347-353), even though its efficacy is doubtful, and the live vaccine is not allowed to be used for layers because of the risk of egg-transmitted infections. Unfortunately, there are still no commercially available preventive strategies against Pullorum disease, unlike Fowl Typhoid. Thus, there is an urgent need for new ways to prevent Fowl Typhoid and Pullorum disease.

Meanwhile, *Salmonella Typhimurium* (hereinbelow, designated as ST) is a zoonotic pathogen which shows no host specificity, unlike SG or SP (Zoobises Report; United Kingdom 2003).

ST is a cause of salmonellosis in poultry, pigs, and cattle, etc. Salmonellosis is caused by *Salmonella* bacteria, an acute or chronic infection of the digestive tract in livestock, and shows the major symptoms of fever, enteritis, and septicemia, occasionally pneumonia, arthritis, abortion, and mastitis. Salmonellosis occurs worldwide, and most frequently during the summer months (T. R. Callaway et al., J. Anim. Sci. 86: E163-E172, 2008). In cattle, typical symptoms include loss of appetite, fever, dark brown diarrhea or bloody mucous stool. Acute infection in calves leads to rapid death, and infection during pregnancy leads to fetal death due to septicemia, resulting in premature abortion. In pigs, salmonellosis is characterized clinically by three major syndromes—acute septicemia, acute enteritis, and chronic enteritis. Acute septicemia occurs in 2-4 month-old piglets, and death usually occurs within 2-4 days after onset of symptoms. Acute enteritis occurs during the fattening period, and is accompanied by diarrhea, high fever, pneumonia, and nervous signs. Discoloration of the skin may occur in some severe cases. Chronic enteritis is accompanied by continuing diarrhea.

Once an outbreak of salmonellosis occurs in poultry, pigs, and cattle, it is difficult to halt with therapeutic agents. The reasons are that *Salmonella* bacteria exhibit a strong resistance to various drugs and live in cells being impermeable to antibiotics. Up to now, there have been no methods for effectively treating salmonellosis caused by ST, including antibiotics.

In addition to livestock, ST causes infections in human via livestock products, leading to *Salmonella* food poisoning. Consumption of infected, improperly cooked livestock products (e.g., meat products, poultry products, eggs and by-products) is a cause of human infection. *Salmonella* food poisoning in human usually involves the prompt onset of headache, fever, abdominal pain, diarrhea, nausea, and vomiting. The symptoms commonly appear within 6-72 hours after the ingestion of the organism, and may persist for as long as 4-7 days or even longer (NSW+HEALTH. 2008 Jan. 14).

According to a report by the CDC (The Centers for Disease Control and Prevention, USA), 16% of human food poisoning outbreaks between 2005 and 2008 attributed to *Salmonella* bacteria, and 18% of them were ST (*Salmonella Typhimurium*). With respect to *Salmonella* food poisoning in human between 1973 and 1984, the implicated food vehicles of transmission were reportedly chicken (5%), beef (19%), pork (7%), dairy products (6%), and turkey (9%). In 1974-1984, the bacterial contamination test on broilers during the slaughter process showed 35% or more of *Salmonella* incidence. In 1983, *Salmonella* was isolated in 50.6% of chicken, 68.8% of turkey, 60% of goose, 11.6% of pork, and 1.5% of beef. Further, a survey carried out in 2007 reported that *salmonella* was found in 5.5% of raw poultry meat and 1.1% of raw pork. In particular, it was revealed that ST commonly originated from contaminated pork, poultry meat, and beef (Centers for Disease Control and Prevention, CDC). A risk assessment conducted by FAO and WHO in 2002 noted that the human incidence of salmonellosis transmitted through eggs and poultry meat appeared to have a linear relationship to the observed *Salmonella* prevalence in poultry. This implies that, by reducing the prevalence of *Salmonella* in poultry, the incidence of salmonellosis in humans will correspondingly fall (*Salmonella* control at the source; World Health Organization. International Food Safety Authorities Network (INFOSAN) Information Note No. 03/2007). Recently, fears about food safety have been spurred by outbreaks of *Salmonella* from products as varied as peanuts, spinach, tomatoes, pistachios, peppers and, most recently, cookie dough (Jane Black and Ed O'Keefe. Overhaul of Food Safety Rules in the Works. Washington Post Staff Writers Wednesday, Jul. 8, 2009).

For these reasons, *Salmonella* infections must be reported in Germany (§6 and §7 of the German law on infectious disease prevention, Infektionsschutzgesetz). Between 1990 and 2005 the number of officially recorded cases decreased from approximately 200,000 cases to approximately 50,000. It is estimated that every fifth person in Germany is a carrier of *Salmonella*. In the USA, there are approximately 40,000 cases of *Salmonella* infection reported each year.

Therefore, there is an urgent need to control ST, which causes salmonellosis in livestock and human. The collaborative efforts of USDA and FDA have led to the development of a number of effective strategies to prevent salmonellosis that causes over 1 million cases of foodborne illness in the United States. In Denmark, conservative estimates from a cost benefit analysis comparing *Salmonella* control costs in the production sector with the overall public health costs of salmonellosis suggest that *Salmonella* control measures saved the Danish society US$ 14.1 million in the year 2001 (*Salmonella* control at the source. World Health Organization. International Food Safety Authorities Network (INFOSAN) Information Note No. 03/2007).

Meanwhile, a bacteriophage is a specialized type of virus that only infects and destroys bacteria, and can self-replicate only inside a host bacteria. A bacteriophage consists of genetic material being single or double-stranded DNA or RNA surrounded by a protein shell. There are three basic structural forms of bacteriophage: an icosahedral (twenty-sided) head with a tail, an icosahedral head without a tail, and a filamentous form. Bacteriophages are classified based on their morphological structure and genetic material. Based on their tail structure, bacteriophages having an icosahedral head and double-stranded, linear DNA as their genetic material are divided into three families: Myoviridae, Siphoviridae, and Podoviridae, which are characterized by contractile, long noncontractile, and short noncontractile tails, respectively. Bacteriophages having an icosahedral head without a tail and RNA or DNA as their genetic material are divided based on their head shape and components, and the presence of a shell. Filamentous bacteriophages having DNA as their genetic material are divided based on their size, shape, shell, and filament components (H. W. Ackermann. Frequency of morphological phage descriptions in the year 2000; Arch Virol, 2001, 146: 843-857; Elizabeth Kutter et al. Bacteriophages biology and application; CRC press).

During infection, a bacteriophage attaches to a bacterium and inserts its genetic material into the cell. After this a bacteriophage follows one of two life cycles, lytic or lysogenic. Lytic bacteriophages take over the machinery of the cell to make phage components. They then destroy or lyse the cell, releasing new phage particles. Lysogenic bacteriophages incorporate their nucleic acid into the chromosome of the host cell and replicate with it as a unit without destroying the cell. Under certain conditions, lysogenic phages can be induced to follow a lytic cycle (Elizabeth Kutter et al. Bacteriophages biology and application. CRC press).

After the discovery of bacteriophages, a great deal of faith was initially placed in their use for infectious-disease therapy. However, when broad spectrum antibiotics came into common use, bacteriophages were seen as unnecessary because of having a specific target spectrum. Nevertheless, the misuse and overuse of antibiotics resulted in rising concerns about antibiotic resistance and harmful effects of residual antibiotics in foods (Cislo, M et al. Bacteriophage treatment of suppurative skin infections. Arch Immunol. Ther. Exp. 1987, 2: 175-183; Kim sung-hun et al., Bacteriophage; New Alternative Antibiotics. Biological Research Information Center, BRIC). In particular, antimicrobial growth promoters (AGPs), added to animal feed to enhance growth, is known to induce antibiotic resistance, and therefore, a ban on the use of AGPs has been recently introduced. In the European Union, the use of all antimicrobial growth promoters (AGPs) was banned from 2006. Korea has banned the use of some AGPs from 2009, and is considering restrictions on the use of all AGPs by 2013-2015.

These growing concerns about the use of antibiotics have led to a resurgence of interest in bacteriophage as an alternative to antibiotics. 7 bacteriophages for control of *E. coli* O157:H are disclosed in U.S. Pat. No. 6,485,902 (applied in 2002-Use of bacteriophages for control of *Escherichia coli* O157). 2 bacteriophages for control of various microorganisms are disclosed in U.S. Pat. No. 6,942,858 (applied by Nymox in 2005). Many companies have been actively trying to develop various products using bacteriophages. EBI food system (Europe) developed a food additive for preventing food poisoning caused by *Listeria monocytogenes*, named Listex-P100, which is the first bacteriophage product approved by the US FDA. A phage-based product, LMP-102 was also developed as a food additive against *Listeria monocytogenes*, approved as GRAS (Generally regarded as safe). In 2007, a phage-based wash produced by OmniLytics was developed to prevent *E. coli* O157 contamination of beef during slaughter, approved by USDA's Food Safety and Inspection Service (FSIS). In Europe, *Clostridium sporogenes* phage NCIMB 30008 and *Clostridium tyrobutiricum* phage NCIMB 30008 were registered as a feed preservative against *Clostridium* contamination of feed in 2003 and 2005, respectively. Such studies show that research into bacteriophages for use as antibiotics against zoonotic pathogens in livestock products is presently ongoing.

However, most of the phage biocontrol studies have focused on the control of *E. coli*, *Listeria*, and *Clostridium*. *Salmonella* is also a zoonotic pathogen, and damages due to this pathogen are significant. As mentioned above, since ST has a multiple drug resistance, nationwide antimicrobial resistance surveillance has been conducted in Korea under an Enforcement Decree of the Act on the Prevention of Contagious Disease (Executive Order 16961), an Enforcement ordinance of the Act on the Prevention of Contagious Disease (Ministry of Health and Welfare's Order 179), and Organization of the National Institute of Health (Executive Order 17164). Accordingly, there is a need for the development of bacteriophages to control *Salmonella*.

DISCLOSURE

Technical Problem

In order to solve the problems including antibiotic resistance due to the misuse and overuse of antibiotics, harmful effects of residual antibiotics in foods, and the problems generated by the use of broad spectrum antibiotics, the present inventors isolated from natural sources a novel *Salmonella* bacteriophage having a specific bactericidal activity against *Salmonella* which causes major diseases in livestock, and identified its morphological, biochemical, and genetic properties. The present inventors found that the bacteriophage has a specific bactericidal activity against *Salmonella typhimurium* (ST), *Salmonella gallinarum* (SG) and *Salmonella pullorum* (SP) without affecting beneficial bacteria, and excellent acid-, heat- and dry-resistance, and thus can be applied to the compositions that can be used for the prevention or treatment of livestock salmonellosis caused by *Salmonella typhimurium*, *Salmonella* food poisoning caused by contaminated livestock products, and infectious diseases caused by *Salmonella gallinarum* or *Salmonella pullorum*, in particular, Fowl typhoid or Pullorum disease, and to various products to control *Salmonella*, such as animal feed additive and drinking water for livestock, barn sanitizers, and cleaners for meat products, thereby completing the present invention.

Technical Solution

It is an object of the present invention to provide a novel bacteriophage having a bactericidal activity against *Salmonella typhimurium*, *Salmonella gallinarum* or *Salmonella pullorum*.

It is another object of the present invention to provide a composition for the prevention or treatment of infectious diseases caused by *Salmonella typhimurium*, *Salmonella gallinarum* or *Salmonella pullorum*, comprising the bacteriophage as an active ingredient, in particular, a composition for the prevention or treatment of the infectious diseases which is used as an antibiotic.

It is still another object of the present invention to provide an animal feed and drinking water, comprising the bacteriophage as an active ingredient.

It is still another object of the present invention to provide a sanitizer and cleaner, comprising the bacteriophage as an active ingredient.

It is still another object of the present invention to provide a method for preventing or treating livestock salmonellosis caused by *Salmonella typhimurium* or *Salmonella* food poisoning caused by contaminated livestock products, using the composition that comprises the bacteriophage as an active ingredient.

It is still another object of the present invention to provide a method for preventing or treating infectious diseases, Fowl Typhoid or Pullorum disease caused by *Salmonella gallinarum* and *Salmonella pullorum*.

Advantageous Effect

The novel bacteriophage of the present invention has a specific bactericidal activity against *Salmonella typhimurium, Salmonella gallinarum*, and *Salmonella pullorum*, and excellent acid-, heat- and dry-resistance. Thus, it can be used for the prevention or treatment of infectious diseases caused by *Salmonella typhimurium, Salmonella gallinarum* or *Salmonella pullorum*, including salmonellosis, *Salmonella* food poisoning, Fowl typhoid or Pullorum disease, and also used for the control of *Salmonella typhimurium, Salmonella gallinarum* and *Salmonella pullorum*.

BEST MODE

In accordance with an aspect, the present invention relates to a novel bacteriophage having a specific bactericidal activity against *Salmonella typhimurium, Salmonella gallinarum* or *Salmonella pullorum*.

The bacteriophage of the present invention belongs to the morphotype of the family Siphoviridae, characterized by isometric capsid and long non-contractile tail, and has a total genome size of 43 kbp and a major structural protein with a size of 40 kDa.

Specifically, the bacteriophage of the present invention has the capability of selectively infecting *Salmonella typhimurium, Salmonella gallinarum* and *Salmonella pullorum*, namely, species specificity.

The bacteriophage of the present invention genetically has a total genome size of 43 kbp, and may include one or more nucleic acid molecules selected from the group consisting of SEQ ID NOs. 1, 2, and 3 within the entire genome, preferably nucleic acid molecules represented by SEQ ID NOs. 1 to 3 within the entire genome.

When the bacteriophage of the present invention is subjected to PCR using one or more primer sets selected from the group consisting of SEQ ID NOs. 4 and 5, SEQ ID NOs. 6 and 7, and SEQ ID NOs. 8 and 9, each PCR product has a size of approximately 1 kbp. Preferably, when PCR is performed using all of the primer sets, each PCR product has a size of approximately 1 kbp.

As used herein, the term "nucleic acid molecule" encompasses DNA (gDNA and cDNA) and RNA molecules, and the term nucleotide, as the basic structural unit of nucleic acids, encompasses natural nucleotides and sugar or base-modified analogues thereof.

The genome of the bacteriophage of the present invention encodes a major structural protein with a size of 40 kDa.

Further, the bacteriophage of the present invention has the biochemical properties of acid- and heat-resistance, in which it can stably retain its infectivity in a wide range of pH environments from pH 2.5 to pH 9.0, and in a high temperature environment from 37° C. to 60° C. In addition, the bacteriophage of the present invention has dry-resistance to stably maintain its infectivity even after high-temperature drying. Such properties of acid-, heat-, and drying-resistance allow application of the bacteriophage of the present invention under various temperature and pH conditions upon the production of prophylactic or therapeutic compositions for livestock diseases caused by ST, SG and SP or human diseases caused by the contaminated livestock.

The present inventors collected sewage samples at chicken slaughterhouses, and isolated therefrom the bacteriophage of the present invention having a specific bactericidal activity against ST, SG and SP and the above characteristics, which was designated as Bacteriophage ΦCJ2 and deposited at the Korean Culture Center of Microorganisms (361-221, Honje 1, Sudaemun, Seoul) on Dec. 17, 2008 under accession number KCCM10976P.

Figure 1:
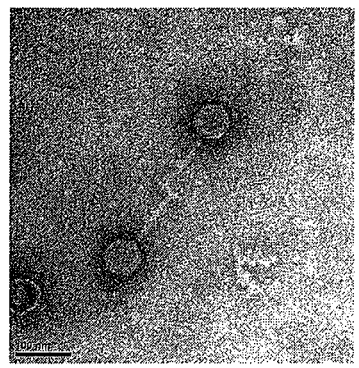
FIG. 1 is an electron microscopy photograph of ΦCJ2, in which ΦCJ2 belongs to the morphotype of the family Siphoviridae, characterized by isometric capsid and long non-contractile tail.

In accordance with the specific Example of the present invention, the present inventors collected sewage samples at chicken slaughterhouses to isolate bacteriophages that lyse the host cell ST, and they confirmed that the bacteriophages are able to lyse SG and SP, specifically (Table 1). Further, they examined the bacteriophage (ΦCJ2) under electron microscope, and found that it belongs to the morphotype of the family Siphoviridae (FIG. 1).

Figure 2:
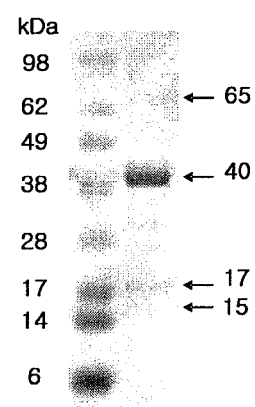
FIG. 2 is the result of SDS-PAGE of the isolated bacteriophage ΦCJ2, in which protein patterns of the bacteriophage are shown, including a major protein of approximately 40 kDa and other proteins of approximately 65 kDa, 17 kDa, and 15 kDa (See-blue plus 2 prestained-standard (Invitrogen) used as marker)

Further, the protein patterns of the bacteriophage (ΦCJ2 were also analyzed, revealing a major structural protein with a size of approximately 40 kDa (FIG. 2).

Figure 3:
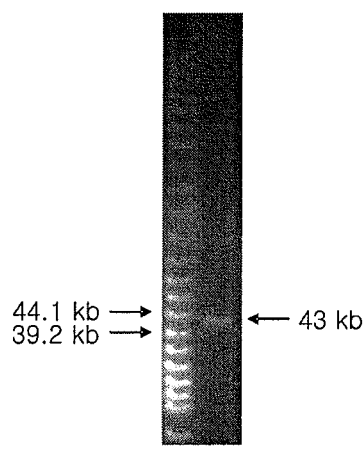
FIG. 3 is the result of PFGE of the isolated bacteriophage ΦCJ2, showing the total genome size of approximately 43 kbp (5 kbp DNA size standard (Bio-rad) as size marker)
Figure 4:
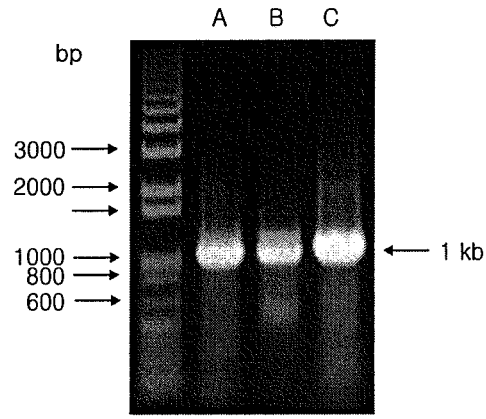
FIG. 4 is the result of PCR, performed using each primer set of ΦCJ2 genomic DNA, in which (A; PCR amplification using primer set of SEQ ID NOs. 4 and 5, B; PCR amplification using primer set of SEQ ID NOs. 6 and 7, C; PCR amplification using primer set of SEQ ID NOs. 8 and 9) each of A, B, and C lanes shows a PCR product of approximately 1 kbp.

Furthermore, the total genome size of the bacteriophage ΦCJ2 was also analyzed, revealing that it has a total genome size of approximately 43 kbp (FIG. 3). The results of analyzing its genetic features showed that the bacteriophage includes nucleic acid sequences represented by SEQ ID NOs. 1 to 3 within the total genome (Example 6). Based on these results, genetic similarity with other species was compared. It was found that the bacteriophage showed very low genetic similarity with the known bacteriophages, indicating that the bacteriophage is a novel bacteriophage (Table 2). More particularly, the ΦCJ2-specific primer set, in particular, SEQ ID NOs. 4 and 5, SEQ ID NOs. 6 and 7, and SEQ ID NOs. 8 and 9, was used to perform PCR. Each PCR product was found to have a size of approximately 1 kbp (FIG. 4).

Further, when SG and SP were infected with ΦCJ2, the phage plaques (clear zone on soft agar created by host cell lysis of one bacteriophage) showed the same size and turbidity.

Figure 6:
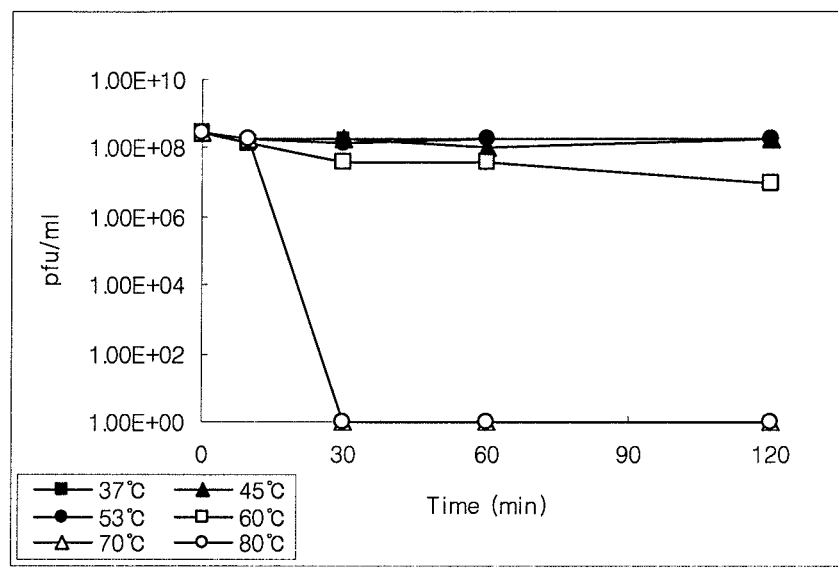
FIG. 6 is the result of heat-resistance test on the bacteriophage ΦCJ2, showing the number of surviving bacteriophage at 37, 45, 53, 60, 70, and 80° C. and a time point of 0, 10, 30, 60, 120 min, in which the bacteriophage ΦCJ2 retains its infectivity even after incubation at 60° C. for 2 hrs, but entirely loses its infectivity after incubation at 70° C. for 10 min.
Figure 7:
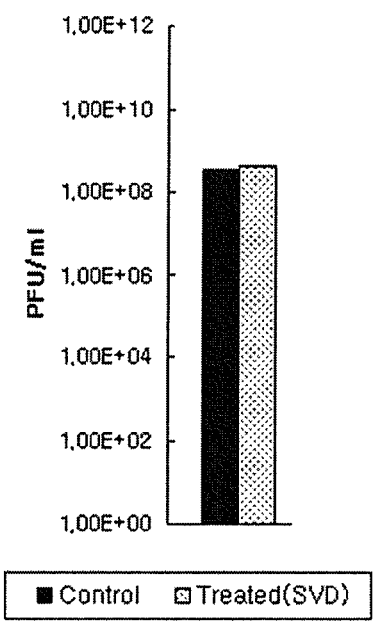
FIG. 7 is the result of dry-resistance test on the bacteriophage ΦCJ2, performed at 60° C. for 120 min using a speed vacuum dryer (SVD), in which changes in viral titers before and after drying were compared to examine the relative stability, and the phage's infectivity was shown not to decrease.

Furthermore, the stability of ΦCJ2 was examined under various temperature and pH conditions, revealing that ΦCJ2 stably maintains its infectivity in a wide range of pH environments from pH 2.5 to pH 9.0 (FIG. 5) and in a high temperature environment from 37° C. to 60° C. (FIG. 6), and even after high-temperature drying at 60° C. for 120 minutes (FIG. 7). These results indicate that the bacteriophage ΦCJ2 of the present invention can be readily applied to various products for the control of *Salmonella*.

In accordance with another aspect, the present invention relates to a composition for the prevention or treatment of infectious diseases caused by one or more selected from the group consisting of *Salmonella typhimurium, Salmonella gallinarum* and *Salmonella pullorum*, comprising the bacteriophage as an active ingredient.

In one preferred embodiment, the therapeutic composition may include an antibiotic.

The bacteriophage of the present invention has a specific bactericidal activity against *Salmonella typhimurium, Salmonella gallinarum* and *Salmonella pullorum*, and thus can be used for the purpose of preventing or treating diseases that are caused by these bacteria. Preferably, examples of the diseases caused by *Salmonella typhimurium* may include salmonellosis or *Salmonella* food poisoning, examples of the diseases caused by *Salmonella gallinarum* may include Fowl typhoid, and examples of the diseases caused by *Salmonella pullorum* may include Pullorum disease, but are not limited thereto.

As used herein, the term "salmonellosis" refers to symptoms caused by *Salmonella* infection, including fever, headache, diarrhea, and vomiting, namely, diseases caused by bacteria of the genus *Salmonella*, which is defined two clinical forms—an acute septicemic form that resembles typhoid fever and an acute gastroenteritis, including enteritis, food poisoning, and acute septicemia.

As used herein, the term "prevention" means all of the actions in which the disease is restrained or retarded by the administration of the composition. As used herein, the term "treatment" means all of the actions in which the disease has taken a turn for the better or been modified favorably by the administration of the composition.

The composition of the present invention comprises ΦCJ2 of $5 \times 10^2$ to $5 \times 10^{12}$ pfu/ml, preferably $1 \times 10^6$ to $1 \times 10^{10}$ pfu/ml.

The composition of the present invention may additionally include a pharmaceutically acceptable carrier, and be formulated together with the carrier to provide foods, medicines, and feed additives.

As used herein, the term "pharmaceutically acceptable carrier" refers to a carrier or diluent that does not cause significant irritation to an organism and does not abrogate the biological activity and properties of the administered compound. For formulation of the composition into a liquid preparation, a pharmaceutically acceptable carrier which is sterile and biocompatible may be used such as saline, sterile water, Ringer's solution, buffered physiological saline, albumin infusion solution, dextrose solution, maltodextrin solution, glycerol, and ethanol. These materials may be used alone or in any combination thereof. If necessary, other conventional additives may be added such as antioxidants, buffers, bacteriostatic agents, and the like. Further, diluents, dispersants, surfactants, binders and lubricants may be additionally added to the composition to prepare injectable formulations such as aqueous solutions, suspensions, and emulsions, or oral formulations such as pills, capsules, granules, or tablets.

The prophylactic or therapeutic compositions of the present invention may be applied or sprayed to the afflicted area, or administered by oral or parenteral routes. The parenteral administration may include intravenous, intraperitoneal, intramuscular, subcutaneous or topical administration.

The dosage suitable for applying, spraying, or administrating the composition of the present invention will depend upon a variety of factors including formulation method, the mode of administration, the age, weight, sex, condition, and diet of the patient or animal being treated, the time of administration, the route of administration, the rate of excretion, and reaction sensitivity. A physician or veterinarian having ordinary skill in the art can readily determine and prescribe the effective amount of the composition required.

Examples of the oral dosage forms suitable for the composition of the present invention include tablets, troches, lozenges, aqueous or emulsive suspensions, powder or granules, emulsions, hard or soft capsules, syrups, or elixirs. For formulation such as tablets and capsules, useful are a binder such as lactose, saccharose, sorbitol, mannitol, starch, amylopectin, cellulose or gelatin, an excipient such as dicalcium phosphate, a disintegrant such as corn starch or sweet potato starch, a lubricant such as magnesium stearate, calcium stearate, sodium stearylfumarate, or polyethylene glycol wax. For capsules, a liquid carrier such as lipid may be further used in addition to the above-mentioned compounds.

For non-oral administration, the composition of the present invention may be formulated into injections for subcutaneous, intravenous, or intramuscular routes, suppositories, or sprays inhalable via the respiratory tract, such as aerosols. Injection preparations may be obtained by dissolving or suspending the composition of the present invention, together with a stabilizer or a buffer, in water and packaging the solution or suspension in ampules or vial units. For sprays, such as aerosol, a propellant for spraying a water-dispersed concentrate or wetting powder may be used in combination with an additive.

As used herein, the term "antibiotic" means any drug that is applied to animals to kill pathogens, and is used herein as a general term for antiseptics, bactericidal agents and antibacterial agents. The animals are mammals including human.

The bacteriophage of the present invention, unlike the conventional antibiotics, has a high specificity to *Salmonella* so as to kill the specific pathogens without affecting beneficial bacteria, and does not induce resistance so that its life cycling is comparatively long.

Figure 9:
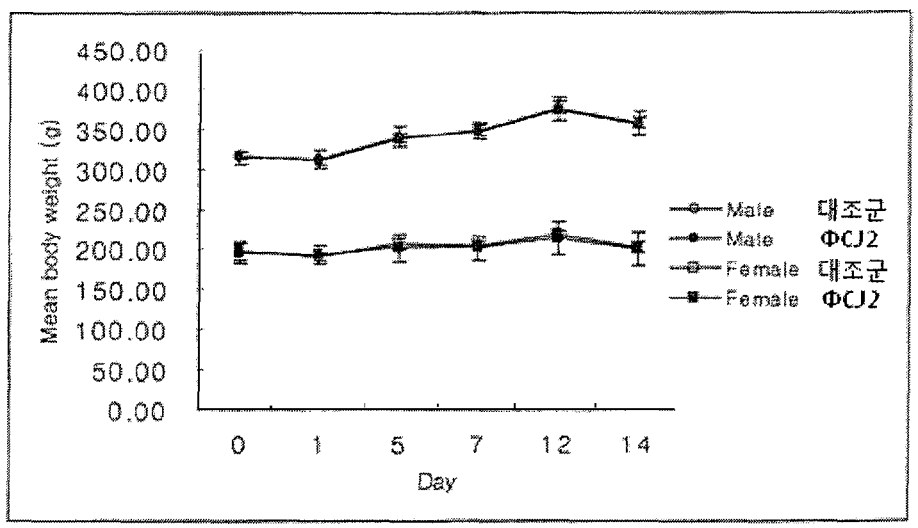
FIG. 9 is the result of single dose intravenous toxicity study of ΦCJ2 in rats, showing changes in body weight (○; male control group treated with the mixed solution of 20 mM Tris-HCl and 2 mM $MgCl_2$, ●; male test group treated with $1\times10^{12}$ pfu of ΦCJ2, □; female control group treated with the mixed solution of 20 mM Tris-HCl and 2 mM $MgCl_2$, ■; female test group treated with $1\times10^{12}$ pfu of ΦCJ2), in which no significant changes in body weight were observed even after 14 days.

In accordance with one specific embodiment of the present invention, single dose oral and intravenous toxicity studies and toxicity study on normal enteric bacteria were performed to evaluate its safety in rats. When a single dose oral toxicity study was performed at a dose level of $1 \times 10^{12}$ pfu of ΦCJ2, there were no marked clinical signs or animal death (Tables 4 and 5). When a single dose intravenous toxicity study was performed at a dose level of $1 \times 10^{12}$ pfu of ΦCJ2, there were also no marked clinical signs or animal death (Tables 6 and 7, and FIG. 9). When a toxicity study on normal enteric bacteria was performed by serial dilution of $1 \times 10^{11}$ pfu/ml of ΦCJ2, it was found that the growth of enteric bacteria was not inhibited even at a maximum dose of ΦCJ2 (Table 8), indicating its safety.

Further, when SG-infected chicken were fed with feed supplemented with ΦCJ2, the ΦCJ2-treated group showed a significantly higher protection rate than the non-treated group. (Table 9), suggesting that ΦCJ2 has prevention and treatment efficacy on SG infection.

In accordance with still another aspect, the present invention relates to an animal feed or drinking water for livestock, comprising the bacteriophage as an active ingredient.

Feed additive antibiotics used in the fishery and livestock industries are used for the purpose of preventing infections, but lead to an increase in resistant strains of bacteria, and residual antibiotics in livestock products may be ingested by humans, contributing to antibiotic resistance in human pathogens and the spread of diseases. In addition, since there are a variety of feed additive antibiotics, the increasing global emergence of multidrug-resistant strains is a serious concern. Therefore, the bacteriophage of the present invention can be used as a feed additive antibiotic that is more ecologically-friendly and able to solve the above problems.

The bacteriophage of the present invention may be separately prepared as a feed additive, and then added to the animal feed, or directly added to the animal feed. The bacteriophage of the present invention may be contained in the animal feed as a liquid or in a dried form, preferably in a dried powder. The drying process may be performed by air drying, natural drying, spray drying, and freeze-drying, but is not limited thereto. The bacteriophage of the present invention may be added as a powder form in an amount of 0.05 to 10% by weight, preferably 0.1 to 2% by weight, based on the weight of animal feed. The animal feed may also include other conventional additives for the long-term preservation, in addition to the bacteriophage of the present invention.

The feed additive of the present invention can additionally include other non-pathogenic microorganisms. The additional microorganism can be selected from a group consisting of *Bacillus subtilis* that can produce protease, lipase and invertase, *Lactobacillus* sp. strain having an ability to decompose organic compounds and physiological activity under anaerobic conditions, filamentous fungi like *Aspergillus oryzae* (J Animal Sci 43: 910-926, 1976) that increases the weight of domestic animals, enhances milk production and helps digestion and absorptiveness of feeds, and yeast like *Saccharomyces cerevisiae* (J Anim Sci 56:735-739, 1983).

The feed comprising ΦCJ2 of the present invention may include plant-based feeds, such as grain, nut, food byproduct, seaweed, fiber, drug byproduct, oil, starch, meal, and grain byproduct, and animal-based feeds such as protein, mineral, fat, single cell protein, zooplankton, and food waste, but is not limited thereto.

The feed additive comprising ΦCJ2 of the present invention may include binders, emulsifiers, and preservatives for the prevention of quality deterioration, amino acids, vitamins, enzymes, probiotics, flavorings, non-protein nitrogen, silicates, buffering agents, coloring agents, extracts, and oligosaccharides for improving process efficiency, and other feed premixtures, but is not limited thereto.

Further, the supply of drinking water mixed with the bacteriophage of the present invention can reduce the number of *Salmonella* bacteria in the intestine of livestock, thereby obtaining *Salmonella*-free livestock.

In accordance with still another aspect, the present invention relates to a sanitizer or a cleaner, comprising the bacteriophage as an active ingredient.

The sanitizer comprising the bacteriophage as an active ingredient can be utilized as a valuable food sanitizer, devoted to food-poisoning prevention. Specifically, in a food industry, it can be used as a food sanitizer or food additive for preventing *Salmonella* infections, and in a livestock industry, it can be also used for the production of *Salmonella*-free livestock. In order to remove *Salmonella*, the sanitizer can be used in sewage disposal plants, and also in poultry barns, slaughterhouses, contaminated areas, and other production facilities, but is not limited thereto.

Further, the cleaner comprising the bacteriophage as an active ingredient can be applied to the contaminated skin, feathers, and other contaminated body parts of living animals, in order to remove *Salmonella*.

In accordance with still another aspect, the present invention relates to a method for treating infectious diseases caused by *Salmonella typhimurium, Salmonella gallinarum* or *Salmonella pullorum*, using the bacteriophage that has a specific bactericidal activity against *Salmonella typhimurium, Salmonella gallinarum*, or *Salmonella pullorum*.

In accordance with still another aspect, the present invention relates to a method for treating infectious diseases caused by *Salmonella typhimurium, Salmonella gallinarum* or *Salmonella pullorum*, using the composition for the prevention or treatment of infectious diseases caused by *Salmonella typhimurium, Salmonella gallinarum* or *Salmonella pullorum*.

The composition of the present invention may be administered to animals in a pharmaceutical formulation or as a component of the animal feed or in their drinking water, preferably administered by mixing into the animal feed as a feed additive.

The composition of the present invention may be administered in a typical manner via any route such as oral or parenteral routes, in particular, oral, rectal, topical, intravenous, intraperitoneal, intramuscular, intraarterial, transdermal, intranasal, and inhalation routes.

The method for treating the diseases of the present invention includes administration of a pharmaceutically effective amount of the composition of the present invention. It will be obvious to those skilled in the art that the total daily dose should be determined through appropriate medical judgment by a physician. The therapeutically effective amount for patients may vary depending on various factors well known in the medical art, including the kind and degree of the response to be achieved, the patient's condition such as age, body weight, state of health, sex, and diet, time and route of administration, the secretion rate of the composition, the time period of therapy, concrete compositions according to whether other agents are used therewith or not, etc.

In accordance with still another aspect, the present invention relates to a method for preventing infectious diseases caused by *Salmonella typhimurium, Salmonella gallinarum* or *Salmonella pullorum*, using the bacteriophage that has a specific bactericidal activity against *Salmonella typhimurium, Salmonella gallinarum*, or *Salmonella pullorum*.

In a preferred embodiment, the present invention has found that the bacteriophage ΦCJ2 can be used to prevent horizontal transmission of SG in commercial layer chickens. In particular, six-week-old chickens, each challenged with $5 \times 10^8$ CFU of SG, cohabited with contact chickens treated with $10^6$ PFU/kg of bacteriophage, prepared in, feed additives, for 7 days before, and 21 days after challenge with SG. Bacteriophage therapy using ΦCJ2 decreased the incidence of organ invasion and produced a significant ($P<0.05$) reduction in mortality in the contact chickens when compared to the untreated contact chickens (see Tables 11 and 12). Considering the fact that the horizontal transmission of *Salmonella* species usually occurs following ingestion of feces of clinically infected chickens or carriers (Jordan, F. T. W. and M. Pattison, Poultry disease, W.B. Saunders Company Ltd., London, U.K. 4: 169-171, 1992), these results suggest that the presence of ΦCJ2 in the intestinal tract of contact chickens might inhibit the SG growth that causes septicemia, as well as provide protection from the horizontal spread of SG due to reduced bacterial shedding and environmental contamination.

In general, the viability of an orally administered bacteriophage may be rapidly reduced under the acidic conditions of the stomach and in the presence of enzymes and other digestive compounds such as bile (Ma, Y. et al., Appl. Environ. Microbiol. 74: 4799-4805, 2008). Thus, a bacteriophage might not survive during gastric passage. However, in the present invention, sufficient ΦCJ2 was identified in feed during the experiment, and was isolated from organs and feces of chickens that received ΦCJ2 in the feed additive, to indicate that ΦCJ2 are stable in feed and did pass through the digestive tract, reach the infection site, and kill the SG. This scenario is plausible because the stomach pH is likely to be much higher after feeding due to the buffering effect of the ingested food (Zhu, H. et al., J. Med. Microbiol. 55: 1265-1270, 2006).

In many poultry industries, live and inactivated killed SG vaccines have been applied to prevent and control the incidence of the disease. Although SG vaccines can reduce clinical signs, they do not provide complete protection against bacterial shedding in SG-infected chickens (Lee, Y. J. et al., Avian Pathol. 36: 495-498, 2007). Therefore, the sole use of SG vaccine in poultry farms may allow chickens to shed bacteria although remaining symptomatically subclinical, which could encourage horizontal transmission and complicate SG eradication. The use of bacteriophage therapy in combination with vaccines or competitive exclusion has proven very successful in limiting *Salmonella* infections in chickens (Methner, U. et al., Int. J. Food Microbiol. 49: 35-42, 1999). Therefore, based on the above results, bacteriophage ΦCJ2 containing feed additives in combination with SG vaccine could be helpful in controlling SG in the poultry industry.

In conclusion, the present invention has demonstrated that bacteriophage therapy using ΦCJ2 could markedly curtailed the mortality and organ invasion in chickens exposed to virulent strains of SG via horizontal transmission. These results provide important insight into preventive and control strategies against *Salmonella* infection and suggest that use of ΦCJ2 may constitute a novel, safe, and effectively plausible alternative to antibiotics for the prevention of *Salmonella* infection in poultry.

Hereinafter, the present invention will be described in more detail with reference to the following Examples. However, these Examples are for illustrative purposes only, and the invention is not intended to be limited by these Examples.

MODE FOR INVENTION

Example 1

Salmonella Bacteriophage Isolation 1-1. Bacteriophage Screening and Single Bacteriophage Isolation 50 ml of sample from chicken slaughterhouse and sewage effluent was transferred to a centrifuge tube, and centrifuged at 4000 rpm for 10 minutes. Then, the supernatant was filtered using a 0.45 µm filter. 18 ml of sample filtrate was mixed with 150 µl of ST shaking culture medium ($OD_{600}$=2) and 2 ml of 10× Luria-Bertani medium (Hereinbelow, designated as LB medium, tryptone 10 g; yeast extract 5 g; NaCl 10 g; final volume to 1 L). The mixture was cultured at 37° C. for 18 hours, and the culture medium was centrifuged at 4000 rpm for 10 minutes. The supernatant was filtered using a 0.2 µm filter. 3 ml of 0.7% agar (w/v) and 150 µl of ST shaking culture medium ($OD_{600}$=2) were mixed, and plated onto LB plate, changed to a solid medium. 10 µl of culture filtrate was spread thereon, and cultured for 18 hours at 37° C. (0.7% agar was used as "top-agar", and the titration of phage lysate was performed on the top-agar, called soft agar overlay method).

The sample culture medium containing the phage lysate was diluted, and mixed with 150 µl of ST shaking culture medium ($OD_{600}$=2), followed by soft agar overlay method, so that single plaques were obtained. Since a single plaque represents one bacteriophage, in order to isolate single bacteriophages, one plaque was added to 400 µl of SM solution (NaCl, 5.8 g; $MgSO_4 7H_2O$, 2 g; 1 M Tris-Cl (pH7.5), 50 ml; $H_2O$, final volume to 1 L), and left for 4 hours at room temperature to isolate single bacteriophages. To purify the bacteriophage in large quantities, 100 µl of supernatant was taken from the single bacteriophage solution, and mixed with 12 ml of 0.7% agar and 500 µl of ST shaking culture medium, followed by soft agar overlay method on LB plate (150 mm diameter). When lysis was completed, 15 ml of SM solution was added to the plate. The plate was gently shaken for 4 hours at room temperature to elute the bacteriophages from the top-agar. The SM solution containing the eluted bacteriophages was recovered, and chloroform was added to 1% of a final volume, mixed well for 10 minutes. The solution was centrifuged at 4000 rpm for 10 minutes. The obtained supernatant was filtered using a 0.2 µm filter, and stored in the refrigerator.

1-2. Large-Scale Batches of Bacteriophage

The selected bacteriophages were cultured in large quantities using ST. ST was shaking-cultured, and an aliquot of $1.5\times10^{10}$ cfu (colony forming unit) was centrifuged at 4000 rpm for 10 minutes, and the pellet was resuspended in 4 ml of SM solution. The bacteriophage of $7.5\times10^7$ pfu (plaque forming unit) was inoculated thereto (MOI: multiplicity of infection=0.005), and left at 37° C. for 20 minutes. The solution was inoculated into 150 ml of LB media, and cultured at 37° C. for 5 hours. Chloroform was added to 1% of a final volume, and the culture solution was shaken for 20 minutes. DNase I and RNase A were added to a final concentration of 1 µg/ml, respectively. The solution was left at 37° C. for 30 minutes. NaCl and PEG (polyethylene glycol) were added to a final concentration of 1 M and 10% (w/v), respectively and left at 4° C. for additional 3 hours. The solution was centrifuged at 4° C. and 12000 rpm for 20 minutes to discard the supernatant. The pellet was resuspended in 5 ml of SM solution, and left at room temperature for 20 minutes. 4 ml of chloroform was added thereto and mixed well, followed by centrifugation at 4° C. and 4000 rpm for 20 minutes. The supernatant was filtered using a 0.2 µm filter, and the bacteriophage was purified by glycerol density gradient ultracentrifugation (density: 40%, 5% glycerol at 35,000 rpm and 4° C. for 1 hour). The purified bacteriophage was designated as Bacteriophage ΦCJ2, and resuspended in 300 µl of SM solution, followed by titration. The bacteriophage ΦCJ2 was deposited at the Korean Culture Center of Microorganisms (361-221, Honje 1, Seodaemun, Seoul) on Dec. 17, 2008 under accession number KCCM10976P.

Example 2

Examination on ΦCJ2 Infection of Salmonella

To examine the lytic activity of the selected bacteriophages on other Salmonella species as well as ST, cross-infection attempts with other Salmonella species were made. As a result, ΦCJ2 did not infect SE (Salmonella enterica Serotype Enteritis), SC (Salmonella enterica Serotype Choleraesuis), SD (Salmonella enterica Serotype Derby) and SA (Salmonella enterica subsp. Arizonae), SB (Salmonella enterica subsp. Bongori). When cross-infection attempts were made with Salmonella species other than ST ATCC14028 strain, the lytic activity was 40% or less, unlike SG and SP. This result suggests that ΦCJ2 is a bacteriophage specific to SG and SP (see Example 11). The results are shown in the following Table 1. The bacteriophages ΦCJ2 that was produced using SG as a host cell showed the same plaque size and plaque turbidity, and the same protein patterns and genome size as those produced using ST as a host cell.

TABLE 1

ΦCJ2 infection of Salmonella

| Sero type | Strain name | Plaque formation | Sero type | Strain name | Plaque formation |
|---|---|---|---|---|---|
| SG | SGSC 2293 | ○ | SC | ATCC 13312 | X |
| SP | SGSC 2295 | ○ | SD | SCSG 2467 | X |
| ST | ATCC 14028 | ○ | SA | ATCC 13314 | X |
| SE | SGSC 2282 | X | SB | ATCC 43975 | X |

*ATCC: The Global Bioresource Center
*SGSC: Salmonella genetic stock center

Example 3

Morphology Examination of Bacteriophage ΦCJ2

The purified ΦCJ2 was diluted in 0.01% gelatin solution, and then fixed in 2.5% glutaraldehyde solution. After the sample was dropped onto a carbon-coated mica plate (ca. 2.5×2.5 mm) and adapted for 10 minutes, it was washed with sterile distilled water. Carbon film was mounted on a copper grid, and stained with 4% uranyl acetate for 30-60 seconds, dried, and examined under JEM-1011 transmission electron microscope (80 kV, magnification of ×120,000-×200,000). As a result, the purified ΦCJ2 was revealed to have morphological characteristics including an isometric capsid and a long non-contractile tail, as shown in FIG. 1, indicating that it belongs to the morphotype of the family Siphoviridae.

Example 4

Protein Pattern Analysis of Bacteriophage ΦCJ2

15 µl of purified ΦCJ2 solution ($10^{11}$ pfu/ml titer) was treated with 3 µl of 5×SDS sample solution, and heated for 5 minutes. The total protein of (ΦCJ2 was run in 4-12% NuPAGE Bis-Tris gel (Invitrogen), and then the gel was stained with coomassie blue for 1 hour at room temperature. As shown in FIG. 2, the protein patterns showed that a band of approximately 40 kDa was observed as a major protein, and bands of approximately 65 kDa, 17 kDa, and 15 kDa were also observed.

Example 5

Total Genomic DNA Size Analysis of Bacteriophage ΦCJ2

Genomic DNA was isolated from the purified ΦCJ2 by ultracentrifugation. Specifically, to the purified ΦCJ2 culture medium, EDTA (ethylenediaminetetraacetic acid (pH8.0)), proteinase K, and SDS (sodium dodecyl sulfate) were added to a final concentration of 20 mM, 50 µg/ml, and 0.5% (w/v), respectively and left at 50° C. for 1 hour. An equal amount of phenol (pH8.0) was added and mixed well, followed by centrifugation at 12000 rpm and room temperature for 10 minutes. The supernatant was mixed well with an equal amount of PC (phenol:chloroform=1:1), followed by centrifugation at 12000 rpm and room temperature for 10 minutes. The supernatant was mixed well with an equal amount of chloroform, followed by centrifugation at 12000 rpm and room temperature for 10 minutes. Again, to the supernatant, added were 1/10 volume of 3 M sodium acetate and two volumes of cold 95% ethanol, and left at −20° C. for 1 hour. After centrifugation at 0° C. and 12000 rpm for 10 minutes, the supernatant was completely removed, and the DNA pellet was dissolved in 50 µl TE (Tris-EDTA (pH 8.0)). The extracted DNA was diluted 10-fold, and its absorbance was measured at $OD_{260}$. After loading 1 µg of total genomic DNA in 1% PFGE (pulse-field gel electrophoresis) agarose gel, electrophoresis was performed using a BIORAD PFGE system program 7 (size range 25-100 kbp; switch time ramp 0.4-2.0 seconds, linear shape; forward voltage 180 V; reverse voltage 120 V) at room temperature for 20 hours. As shown in FIG. 3, ΦCJ2 had a genomic DNA size of approximately 43 kbp.

Example 6

Genetic Analysis of Bacteriophage ΦCJ2

To analyze genetic features of the purified ΦCJ2, 5 µg of genomic DNA of ΦCJ2 was treated with the restriction enzyme EcoR V. The vector pCL (Promega) was digested with Sma I, and treated with CIP (calf intestinal alkaline phosphatase). The digested genomic DNA and vector were mixed in a ratio of 3:1, and ligated at 16° C. for 5 hours. The ligation product was transformed into E. coli DH5α. The transformed cells were plated on LB plate containing spectinomycin and X-gal (5-bromo-4-chloro-3-indolyl-beta-D-galactopyranoside) for blue/white selection, so as to select three colonies. The selected colony was shaking-cultured in a culture medium containing spectinomycin for 16 hours. Then, plasmids were extracted using a plasmid purification kit (Promega). The cloning of the plasmids was confirmed by PCR using a primer set of M13 forward and M13 reverse, and insertion fragments of 1 kbp or more were selected, and their base sequence was analyzed using the primer set of M13 forward and M13 reverse. As shown in SEQ ID NOs. 1, 2 and 3, the size was approximately 3.1 kbp, 1.7 kbp and 800 bp, respectively. Sequence similarity was analyzed using a NCBI blastx program, and the results are shown in the following Table 2.

As shown in the following Table 2, ΦCJ2 showed 90% sequence similarity with BPKS7gp07 of Salmonella phage KS7 and with the coat protein of SETP3 in the forward sequence of SEQ ID NO. 1. The backward sequence of SEQ ID NO. 1 also showed 75% and 66% sequence similarity with BPKS7gp04 and SPSV3_gp41 of Salmonella phage KS7 and phage SET3, respectively. In SEQ ID NO. 2, the forward sequence showed 91% sequence similarity with the hypothetical protein SPSV3_gp02 of Salmonella phage SETP3, and the backward sequence showed 94% sequence similarity with the tail component protein of Salmonella phage SETP3. The sequence of SEQ ID NO. 3 also showed 69% sequence similarity with BPKS7gp41 of Salmonella phage KS7 and DNA polymerase of phage SETP3. The base sequence analysis of SEQ ID NOs. 1 2 and 3 by NCBI blastn program resulted in 60-70% sequence similarity with Salmonella phage KS7 and SETP3. However, they are not completely identical to each other, suggesting that ΦCJ2 is a novel bacteriophage that infects Salmonella.

TABLE 2

Sequence similarity comparison of ΦCJ2 with other bacteriophages

| | organism | protein | Accession number | Subject location | Query location | identities | E value |
|---|---|---|---|---|---|---|---|
| 1 | Salmonella phage KS7 | hypothetical protein BPKS7gp09 | AAW51212 | 123-349 | 3-683 | 205/227 (90%) | 7e−115 |
| | Salmonella phage SETP3 | putative coat protein | ABN47366 | 123-349 | 3-683 | 203/227 (89%) | 6e−114 |
| | Salmonella phage SETP3 | hypothetical protein SPSV3_gp41 | ABN47370 | 1-169 | 1630-2136 | 112/169 (66%) | 1e−49 |
| | Salmonella phage KS7 | hypothetical protein BPKS7gp04 | AAW51207 | 1-199 | 2142-2747 | 153/202 (75%) | 2e−79 |
| 2 | Salmonella phage KS7 | hypothetical protein | AAW51256 | 1-433 | 372-1670 | 402/433 (92%) | 0.0 |
| | Salmonella phage SETP3 | tail component protein | ABN47332 | 9-322 | 729-1670 | 296/314 (94%) | 5e−164 |
| | Bacteriophage MB78 | hypothetical protein | CAB36893 | 21-287 | 3-803 | 248/267 (92%) | 3e−143 |
| | Salmonella phage SETP3 | hypothetical protein SPSV3_gp02 | ABN47331 | 21-267 | 3-743 | 225/247 (91%) | 6e−129 |

TABLE 2-continued

Sequence similarity comparison of ΦCJ2 with other bacteriophages

| organism | protein | Accession number | Subject location | Query location | identities | E value |
|---|---|---|---|---|---|---|
| 3 Salmonella phage KS7 | hypothetical protein BPKS7gp41 | AAW51246 | 176-417 | 789-1 | 182/263 (69%) | 1e-87 |
| Salmonella phage SETP3 | DNA polymerase | ABN47339 | 176-417 | 789-1 | 182/263 (69%) | 2e-87 |

Example 7

Construction of ΦCJ2-Specific Primer Sequence

To identify ΦCJ2, ΦCJ2-specific primers were constructed on the basis of SEQ ID NOs. 1, 2 and 3. PCR was performed using each primer set of SEQ ID NOs. 4 and 5, SEQ ID NOs. 6 and 7, and SEQ ID NOs. 8 and 9. 0.1 μg of genomic DNA of bacteriophage and 0.5 μmol of primer were added to premix (Bioneer), and the final volume was adjusted to 20 μl. PCR was performed with 30 cycles of denaturation; 94° C. for 1 min, annealing; 53° C. for 1 min, and polymerization; 72° C. for 1 min. When SEQ ID NOs. 4 and 5, SEQ ID NOs. 6 and 7, and SEQ ID NOs. 8 and 9 were used as primer set, all PCR products had a size of approximately 1 kbp. The results are shown in FIG. 4.

Example 8 pH Stability Test on Bacteriophage

Figure 5:
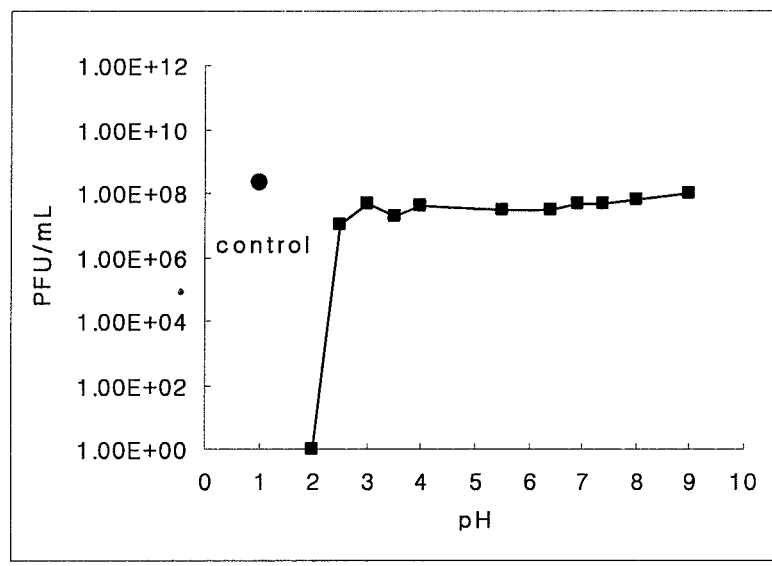
FIG. 5 is the result of acid-resistance test on the bacteriophage ΦCJ2, showing the number of surviving bacteriophage at pH 2.1, 2.5, 3.0, 3.5, 4.0, 5.5, 6.4, 6.9, 7.4, 8.0, and 9.0, in which the bacteriophage ΦCJ2 retains its infectivity to pH 2.5, but entirely loses its infectivity at pH 2.1, as compared to control.

To test the stability of ΦCJ2 in a low-pH environment like the chicken stomach, the stability test was performed in a wide range of pH (pH 2.1, 2.5, 3.0, 3.5, 4.0, 5.5, 6.4, 6.9, 7.4, 8.2, 9.0). Various pH solutions (Sodium acetate buffer (pH 2.1, pH 4.0, pH 5.5, pH 6.4)), Sodium citrate buffer (pH 2.5, pH 3.0, pH 3.5), Sodium phosphate buffer (pH 6.9, pH 7.4), Tris-HCl (pH 8.2, pH 9.0)) were prepared at a concentration of 2 M. 100 μl of pH solution was mixed with an equal amount of bacteriophage solution ($1.0 \times 10^{11}$ pfu/ml) to the concentration of each pH solution to 1 M, and left at room temperature for 1 hour. The reaction solution was serially diluted, and 10 μl of each diluted sample was cultured at 37° C. for 18 hours by soft agar overlay method, and the titration of phage lysates was performed. Changes in the titers according to pH difference were compared to examine the relative stability. The results showed that the bacteriophage did not lose its infectivity and maintained stability to pH 2.5. However, it lost its infectivity at pH 2.1. The results are shown in FIG. 5.

Example 9

Heat Stability Test on Bacteriophage

To test stability of bacteriophage to heat generated during formulation process when used as a feed additive, the following experiment was performed. 200 μl of ΦCJ2 solution ($1.0 \times 10^{11}$ pfu/ml) was left at 37° C., 45° C., 53° C., 60° C., 70° C., and 80° C. for 0 min, 10 min, 30 min, 60 min, and 120 min, respectively. The solution was serially diluted, and 10 μl of each diluted sample was cultured at 37° C. for 18 hours by soft agar overlay method, and the titration of phage lysates was performed. Changes in the titers according to temperature and exposure time were compared to examine the relative stability. The results showed that the bacteriophage retained its infectivity following incubation at 60° C. for 2 hours. However, the bacteriophage rapidly lost its infectivity following incubation at 70° C. or higher for 10 minutes. The results are shown in FIG. 6.

Example 10

Dry Stability Test on Bacteriophage

To test stability of bacteriophage under the dry condition during formulation process when used as a feed additive, the following experiment was performed. On the basis of the results of heat stability test, the experiment was performed under high-temperature drying conditions (at 60° C. for 120 min). 200 μl of ΦCJ2 solution ($1.0 \times 10^{11}$ pfu/ml) was dried using a Speed vacuum (Speed-Vacuum Concentrator 5301, Eppendorf). The obtained pellet was completely resuspended in an equal amount of SM solution at 4° C. for one day. The solution was serially diluted, and 10 μl of each diluted sample was cultured at 37° C. for 18 hours by soft agar overlay method, and the titration of phage lysates was performed. Changes in the titers before and after drying were compared to examine the relative stability. The results showed that its activity was not reduced. The results are shown in FIG. 7.

Example 11

Examination on Bacteriophage Infection of Wild-Type Strain

The lytic activity of bacteriophage ΦCJ2 was tested for each 20 strains of the Korean wild-type SG and SP, isolated by Laboratory of Avian Diseases, College of Veterinary Medicine, Seoul National University, in addition to SG (SG SGSC2293), SP (SP SGSC2295) and ST (ST ATCC14028) used in the present invention. 150 μA of each strain shaking culture medium ($OD_{600}$=2) was mixed, and 10 μl of ΦCJ2 solution ($10^{10}$ pfu/ml) was cultured at 37° C. for 18 hours by soft agar overlay method, and the plaque formation was examined. It was found that the bacteriophage ΦCJ2 showed 100% lytic activity on the wild-type SG and SP. The results are shown in the following Table 3. Its lytic activity on 20 strains of wild-type ST was also examined, revealing that the bacteriophage ΦCJ2 showed 80% lytic activity (not shown in the following Table 3). Thus, the results suggest that ΦCJ2 is a bacteriophage being specific to SG, SP and ST.

TABLE 3

Lytic activity on wild-type SG, SP and ST

| Serotype | Strain name | plaque formation |
|---|---|---|
| SG | SNU SG1 | o |
|  | SNU SG2 | o |

TABLE 3-continued

Lytic activity on wild-type SG, SP and ST

| Serotype | Strain name | plaque formation |
|---|---|---|
| | SNU SG3 | ○ |
| | SNU SG4 | ○ |
| | SNU SG5 | ○ |
| | SNU SG6 | ○ |
| | SNU SG7 | ○ |
| | SNU SG8 | ○ |
| | SNU SG9 | ○ |
| | SNU SG10 | ○ |
| | SNU SG11 | ○ |
| | SNU SG12 | ○ |
| | SNU SG13 | ○ |
| | SNU SG14 | ○ |
| | SNU SG15 | ○ |
| | SCSG 9184 | ○ |
| | SCSG 2292 | ○ |
| | SCSG 2293 | ○ |
| | SCSG 2744 | ○ |
| | SCSG 2296 | ○ |
| ST | SNU ST1 | x |
| | SNU ST2 | ○ |
| | SNU ST3 | x |
| | SNU ST4 | ○ |
| | SNU ST7 | ○ |
| | SNU ST8 | ○ |
| | SNU ST11 | ○ |
| | SNU ST12 | ○ |
| | SNU ST13 | ○ |
| | SNU ST14 | ○ |
| | SNU ST17 | ○ |
| | SNU ST18 | x |
| | SNU ST19 | ○ |
| | SNU ST20 | ○ |
| | SNU ST25 | ○ |
| | SNU ST26 | ○ |
| | SNU ST37 | ○ |
| | SNU ST38 | x |
| | SNU ST41 | ○ |
| | SNU ST42 | ○ |
| SP | SNU SP 1 | ○ |
| | SNU SP 4 | ○ |
| | SNU SP 5 | ○ |
| | SNU SP 8 | ○ |
| | SNU SP 11 | ○ |
| | SCSG 2294 | ○ |
| | SCSG 2295 | ○ |
| | SCSG 2737 | ○ |
| | SCSG 2739 | ○ |
| | SCSG 2742 | ○ |
| | SCSG 2743 | ○ |
| | SCSG 2745 | ○ |
| | SCSG 2751 | ○ |
| | SCSG 4663 | ○ |
| | SCSG 4664 | ○ |
| | SCSG 4665 | ○ |
| | SCSG 4666 | ○ |
| | SCSGSA1684 | ○ |

\* SG/SP source: Laboratory of Avian Diseases, College of Veterinary Medicine, Seoul National University
\* SGSC: *Salmonella* genetic stock center

Example 12

Toxicity Test of Bacteriophage

To evaluate ΦCJ2 safety in rats, toxicity studies were performed. Single dose oral and intravenous toxicity studies and toxicity study on normal enteric bacteria were performed.

Figure 8:
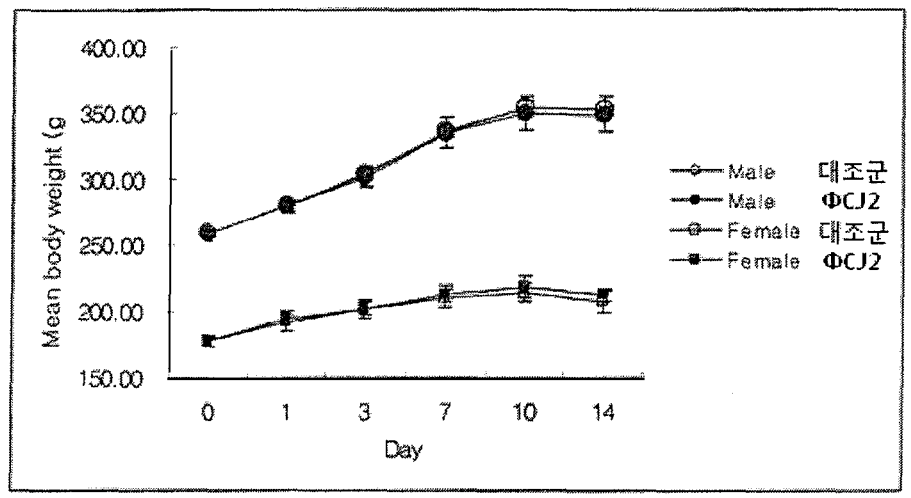
FIG. 8 is the result of single dose oral toxicity study of ΦCJ2 in rats, showing changes in body weight (○; male control group treated with the mixed solution of 20 mM Tris-HCl and 2 mM $MgCl_2$, ●; male test group treated with $1\times10^{12}$ pfu of ΦCJ2, □; female control group treated with the mixed solution of 20 mM Tris-HCl and 2 mM $MgCl_2$, ■; female test group treated with $1\times10^{12}$ pfu of ΦCJ2), in which no significant changes in body weight were observed even after 14 days.

To examine acute toxicity in rats and mortality rate by single oral administration, single dose oral toxicity study was performed. Male and female (12 rats for each), 7-week-old, specific pathogen-free (SPF) rats were fasted one day before ΦCJ2 administration. On administration day, $1 \times 10^{12}$ pfu of ΦCJ2 was administered to male and female rats (6 rats for each) via an oral sonde, and a mixed solution of 20 mM Tris-HCl and 2 mM $MgCl_2$ was orally administered to 6 rats as a control group, after 4 hrs, to start refeeding. On administration day, the rats were examined 30 min after administration, and every 4 hours. For 14 days, clinical signs were examined and recorded once a day. As a result, there was no animal death, and clinical signs due to ΦCJ2 toxicity were not observed. The results are shown in Tables 4 and 5. Changes in body weight were measured and recorded before administration, and 1, 3, 7, 10 and 14 days after administration. As shown in FIG. 8, there were no significant changes in body weight, as compared to control group. The results indicate that ΦCJ2 does not induce loss of appetite or toxic signs which cause changes in body weight. The surviving rats were autopsied and examined for gross lesions. No gross abnormalities were observed.

TABLE 4

Incidence of death after oral administration of ΦCJ2

| Sex | Dose (pfu) | Hours after treatment | | | | | Days after treatment | | | | | | | | | | | | | | Final mortality |
|---|---|---|---|---|---|---|---|---|---|---|---|---|---|---|---|---|---|---|---|---|---|
| | | 0.5 | 1 | 2 | 3 | 4 | 1 | 2 | 3 | 4 | 5 | 6 | 7 | 8 | 9 | 10 | 11 | 12 | 13 | 14 | |
| Male | Control | 0 | 0 | 0 | 0 | 0 | 0 | 0 | 0 | 0 | 0 | 0 | 0 | 0 | 0 | 0 | 0 | 0 | 0 | 0 | 0/6 |
| | $1 \times 10^{12}$ | 0 | 0 | 0 | 0 | 0 | 0 | 0 | 0 | 0 | 0 | 0 | 0 | 0 | 0 | 0 | 0 | 0 | 0 | 0 | |
| Female | Control | 0 | 0 | 0 | 0 | 0 | 0 | 0 | 0 | 0 | 0 | 0 | 0 | 0 | 0 | 0 | 0 | 0 | 0 | 0 | 0/6 |
| | $1 \times 10^{12}$ | 0 | 0 | 0 | 0 | 0 | 0 | 0 | 0 | 0 | 0 | 0 | 0 | 0 | 0 | 0 | 0 | 0 | 0 | 0 | |

TABLE 5

Clinical signs after oral administration of ΦCJ2

| Sex | Dose (pfu) | Final mortality Male | Female | Clinical signs Male | Female |
|---|---|---|---|---|---|
| Male | Control | 0/6[a] | 0/6 | 0/6[b] | 0/6 |
|  | 1 × 10^12 | 0/6 | 0/6 | 0/6 | 0/6 |
| Female | Control | 0/6 | 0/6 | 0/6 | 0/6 |
|  | 1 × 10^12 | 0/6 | 0/6 | 0/6 | 0/6 |

[a]Values are expressed as number of dead animal/total number of animals.
[b]Values are expressed as number of animals with clinical signs/total number of animals.

To examine bacteriophage toxicity in blood, single dose intravenous toxicity study was performed. Male and female (10 rats for each), 7-week-old, specific pathogen-free (SPF) rats were subjected to the experiment. On administration day, 1×10$^{12}$ pfu of ΦCJ2 was administered to the lateral tail veins of male and female rats (5 rats for each) using a 3 ml syringe, and a mixed solution of 20 mM Tris-HCl and 2 mM MgCl$_2$ was administered into the lateral tail veins of 5 rats as a control group. Under the same conditions as oral toxicity study, animal death and clinical signs, changes in body weight and the result of necropsy were examined, and shown in Tables 6 and 7, and FIG. 9, respectively. During the experimental period, there was no animal death, and clinical signs due to ΦCJ2 toxicity were not observed. Further, there were no significant changes in body weight, as compared to control group. The results indicate that ΦCJ2 does not induce toxicity. Furthermore, the surviving rats were autopsied and examined for gross lesions. No gross abnormalities were observed.

TABLE 6

Incidence of death after intravenous administration of ΦCJ2

| Sex | Dose (pfu) | Hours after treatment 0.5 | 1 | 2 | 3 | 4 | Days after treatment 1 | 2 | 3 | 4 | 5 | 6 | 7 | 8 | 9 | 10 | 11 | 12 | 13 | 14 | Final mortality |
|---|---|---|---|---|---|---|---|---|---|---|---|---|---|---|---|---|---|---|---|---|---|
| Male | Control | 0 | 0 | 0 | 0 | 0 | 0 | 0 | 0 | 0 | 0 | 0 | 0 | 0 | 0 | 0 | 0 | 0 | 0 | 0 | 0/5 |
|  | 1 × 10^12 | 0 | 0 | 0 | 0 | 0 | 0 | 0 | 0 | 0 | 0 | 0 | 0 | 0 | 0 | 0 | 0 | 0 | 0 | 0 |  |
| Female | Control | 0 | 0 | 0 | 0 | 0 | 0 | 0 | 0 | 0 | 0 | 0 | 0 | 0 | 0 | 0 | 0 | 0 | 0 | 0 | 0/5 |
|  | 1 × 10^12 | 0 | 0 | 0 | 0 | 0 | 0 | 0 | 0 | 0 | 0 | 0 | 0 | 0 | 0 | 0 | 0 | 0 | 0 | 0 |  |

TABLE 7

Clinical signs after intravenous administration of ΦCJ2

| Sex | Dose (pfu) | Final mortality Male | Female | Clinical signs Male | Female |
|---|---|---|---|---|---|
| Male | Control | 0/5[a] | 0/5 | 0/5[b] | 0/5 |
|  | 1 × 10^12 | 0/5 | 0/5 | 0/5 | 0/5 |
| Female | Control | 0/5 | 0/5 | 0/5 | 0/5 |
|  | 1 × 10^12 | 0/5 | 0/5 | 0/5 | 0/5 |

[a]Values are expressed as number of dead animal/total number of animals.
[b]Values are expressed as number of animals with clinical signs/total number of animals.

To examine the ΦCJ2 toxicity on normal enteric bacteria, 9 species of normal enteric bacteria, identified in toxicity test guidelines for animal drugs, [*Bacteroides fragilis* (ATCC25285), *Bacteroides ovatus* (ATCC8483), *Fusobacterium prausnitzii* (ATCC 27766), *Bifidobacterium Longum* (KACC 20597, ATCC15697), *Clostridium perfringens* (ATDD13124), *Peptococcus anaerobius* (ATCC27337), *Enterococcus faecalis* (KACC 11304, ATCC35308), *Lactovacillus acidophilus* (KACC12419, ATCC 4356), *Escherichia coli* (KACC 10005, ATCC 35607)] were subjected to the toxicity study. 1×10$^{11}$ pfu/ml of ΦCJ2 was serially diluted and 100 μl of dilution was aliquoted to a 96 well plate. Then, culture media of 9 species were added to the plate, and cultured under the predetermined conditions for 18-48 hrs. Cell density was measured to determine the minimal inhibitory concentration. It was found that the growth of enteric bacteria was not inhibited even at the maximum concentration of ΦCJ2, shown in Table 8. The results indicate that ΦCJ2 does not affect normal enteric bacteria.

TABLE 8

| Microorganism | Media | Culture conditions | ΦCJ2 | MIC |
|---|---|---|---|---|
| *Bacteroides fragilis* (ATCC 25285) | Thioglycollate anaerobic | 37° C. Strict anaerobic (GasPak) | 1×10$^2$~1 × 10$^{10}$ CFU/ml by 10-fold dilution | Not determined (ND) |
| *Bacteroides ovatus* (ATCC 8483) | Thioglycollate anaerobic | 37° C. Strict anaerobic (GasPak) |  | (ND) |
| *Fusobacterium prausnitzii* (ATCC 27766) | Thioglycollate anaerobic | 37° C. Strict anaerobic (GasPak) |  | (ND) |
| *Bifidobacterium Longum* (KACC 20597, ATCC 15697) | Reinforced clostridial medium anaerobic | 37° C. Strict anaerobic (GasPak) |  | (ND) |
| *Clostridium perfringens* (ATCC 13124) | Reinforced clostridial medium anaerobic | 37° C. Strict anaerobic (GasPak) |  | (ND) |
| *Peptococcus anaerobius* (ATCC 27337) | Thioglycollate anaerobic | 37° C. Strict anaerobic (GasPak) |  | (ND) |
| *Enterococcus faecalis* (KACC 11304, ATCC 35308) | Muller Hinton Broth | 37° C. aerobic |  | (ND) |
| *Lactobacillus acidophilus* (KACC 12419, ATCC 4356) | Lactobacilli MRS Broth | 37° C. 5% CO$_2$ (Gas Pak) |  | (ND) |
| *Escherichia coli* (KACC 10005 ATCC 35607) | Muller Hinton broth | 37° C. aerobic |  | (ND) |

Example 13

Therapeutic Efficacy Test on Bacteriophage

In order to evaluate the efficacy of ΦCJ2 on the treatment of ST, SG and SP, the following efficacy test was performed in chickens.

20 brown layers (1-day-old) were divided into 10 test groups with 10 layers (ΦCJ2 treated group+non-treated challenged group 1). For 1 week, the test chicks were fed with feed supplemented with $10^7$ pfu of ΦCJ2 (per g) and drinking water supplemented with $10^7$ pfu of ΦCJ2 (per ml). At 1 week, $10^6$ cfu of SG0197 (per chick) and $10^7$ pfu (MOI=10) of each phage were mixed with 500 μl of TSB, and left in ice for 1 hour or less, followed by oral administration. The mortality rate was examined for 2 weeks. The surviving chicks were subjected to necropsy and examined for gross lesions, and the bacteria were isolated. As shown in Table 9, it was found that the ΦCJ2-treated group showed a significantly higher protection rate ($P<0.05$) than the non-treated group.

TABLE 9

Efficacy test of ΦCJ2 in chickens

| | ΦCJ2-treated & SG challenged group | SG challenged without ΦCJ2-treatment group |
|---|---|---|
| Survival | 9 | 3 |
| Mortality rate | 10% | 70% |
| Clinical signs | 1/9 | 1/3 |
| SG reisolation | 0/9 | 0/3 |
| Protection rate | 80% | 20% |

Example 14

Prophylactic Efficacy Test on Bacteriophage

In order to evaluate the efficacy of ΦCJ2 on the prevention of SG, the following efficacy test was performed in chickens.

Six-week-old commercial layer chickens were obtained from a *Salmonella*-free chicken flock and were housed in a cage under strict biosecurity. The chickens were negative for antibodies against *Salmonella Enteritidis* and *Salmonella Typhimurium* by enzyme linked-immunosorbent assay (Biocheck, Foster City, Calif.) and against SG by a rapid serum agglutination (RSA) test. All experiments were carried out according to protocols approved by the Institutional Animal Care and Use Committee of the Konkuk University, Seoul, Korea.

*Salmonella Gallinarum* 2293 (SG2293), purchased from *Salmonella* Genetic Stock Center (Calgary, AB, Canada), was used and was designated as SG. Inocula for challenge were prepared from 18-24 hr Luria-Bertani (LB) broth cultures maintained at 37° C. After overnight incubation, the broth was centrifuged at 2500×g for 10 min and the bacterial pellet was suspended and serially diluted in sterile phosphate-buffered saline (pH 7.2). Bacterial enumeration of the suspension was performed using LB agar. The SG challenge strain is virulent for chickens and the 50% lethal dose of SG challenge strain, in challenged and contact chickens, was determined to be $5×10^6$ CFU/ml and $5×10^8$ CFU/ml, respectively.

Six-week-old commercial layer chickens (n=175) were divided into three experimental groups (Table 10).

TABLE 10

Experimental design

| Group | | Number of chickens | Treatment |
|---|---|---|---|
| 1 | SG challenged | 35 | SG challenged[A] with ΦCJ2 treatment[B] |
| | SG free[C] | 35 | Only ΦCJ2 treated (SG free) |
| 2 | SG challenged | 35 | Only SG challenged (ΦCJ2 free) |
| | SG free[C] | 35 | Free of both SG and ΦCJ2 |
| 3 | Negative control[D] | 35 | Free of both SG and ΦCJ2 |

[A]Six-week-old chickens were orally challenged with SG (LP-93 strain) at a concentration of $5 × 10^8$ CFU/bird.
[B]Chickens were treated with ΦCJ2 as a feed additive at a concentration of $10^6$ PFU/kg.
[C]Chickens were housed in the same cage with SG challenged chickens.
[D]Chickens in negative control were isolated from other groups.

Group 1 contained 70 birds; 35 birds were each orally-challenged with $5×10^8$ CFUs of SG, then all the 70 birds were treated with $10^6$ PFU/kg of ΦCJ2, contained in the poultry feed, for 7 days before and 21 days after the SG challenge. Group 2 contained 70 birds; 35 birds were orally challenged with SG and 35 contact birds did not receive any treatment. In order to investigate horizontal transmission, stool samples from SG challenged and SG free birds were collected from the chickens of each Group and the presence of SG therein was detected. Group 3 contained 35 birds that were free of both SG and ΦCJ2 and was served as an unchallenged and untreated negative control. The chickens of Group 3 were raised separately without contact with the other groups.

To avoid a high density of chickens in any cage, which could change the dynamics of the spread of *Salmonella*, 70 chickens of groups 1 and 2 were divided into 4 cages, respectively. Forty chickens were housed in two cages (Cage 1=10 challenged chickens+10 contact chickens [n=20]; Cage 2=10 challenged chickens+10 contact chickens [n=20]) to observe mortality caused by SG horizontal transmission. Thirty chickens were housed in two cages (Cage 3=7 challenged chickens+8 contact chickens [n=15]; Cage 4=8 challenged chickens+7 contact chickens [n=15]) to observe the re-isolation rate of SG. The birds were monitored for mortality daily for 21 days after challenge. Sera samples were collected for SG antibody detection using RSA at 2 wk after challenge. At 7, 14, and 21 days postchallenge (dpc), the liver, spleen, and cecum were aseptically collected from 10 chickens per group (five challenged and five contact chickens) to re-isolate the SG challenge strain.

Bacteriologic analysis was performed as follows: An approximately 1 g tissue sample was macerated in 10 ml of buffered peptone water broth (Difco, Detroit, Mich.) and incubated overnight at 37° C. A 0.1-ml volume of culture was inoculated into Rappaport-Vassiliadis broth (Difco) and incubated at 37° C. for 48 hr prior to plating on xylose-lysine desoxycholate (Difco) and brilliant green agar (Difco). Plates were incubated at 37° C. for 24 hr and examined for the presence of SG. The identity of the challenge strain was confirmed using *Salmonella* antiserum (Difco).

Serologic tests were carried out as follows: SG antibodies were detected by the RSA plate test used as an authorized method in Korea (Choi Y.-J. et al. Korean J. Vet Serv. 23(4):

349-360, 2000). The serum plate agglutination antigen was prepared with a homologous SG strain as described previously (Gast, R. K., Poult. Sci. 76: 17-23. 1997). For the reaction, 30 ml of antigen was mixed with an equal volume of serum on a clean, white tile marked into squares of about 3×3 cm². The mixture was observed for agglutination after 2 min of constant rotation. A positive reaction was indicated by easily visible clumping of the antigen within 2 min.

Statistical analysis was performed as follows: Mortality rate in chickens and SG re-isolation rate in organs were analyzed using a one-tailed Fisher's exact test. A P-value <0.05 was considered to be statistically significant.

In the serologic test, all the chickens were determined to be *Salmonella* seronegative prior to challenge and were demonstrated to be efficiently seroconverted to SG at 2 weeks after bacterial challenge, suggesting that horizontal transmission of SG had occurred (Table 11).

Figure 10:
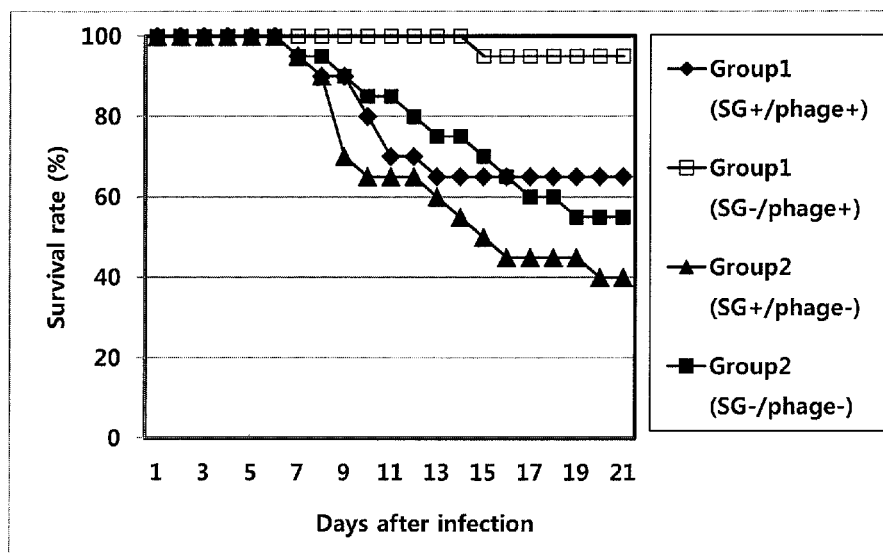
FIG. 10 is the results of comparing efficacy of ΦCJ2 on survival rate of SG challenged and contact chickens. Six-week-old chickens, each challenged with 5×10$^8$ CFUs of SG, cohabited with contact chickens treated with 10$^6$ PFU/kg of ΦCJ2 prepared in feed additives for 7 days before, and 21 days after challenge with SG. Mortality was observed for 3 week after challenge. Asterisk (*) indicates significant difference (P<0.05) between ΦCJ2-treated and untreated contact chickens.

Mortality of challenged chickens was first observed at 7 dpc (FIG. 10). Mortality rates of challenged and contact chickens that did not received with ΦCJ2 were 55% and 45%, but challenged and contact chickens treated with ΦCJ2 were 40% and 5%, respectively (Table 11 and FIG. 10). The mortality rate of the contact chickens treated with ΦCJ2 was significantly decreased (P<0.05) when compared with that of the untreated contact chickens. In the re-isolation study, untreated contact chickens displayed a 40% re-isolation rate of the SG challenge strain in the liver and spleen, while the challenge strain was not isolated in contact chickens treated with ΦCJ2 at 2 weeks post-challenge (Table 12).

TABLE 12

Effect of ΦCJ2 on organ invasion caused by horizontal transmission of SG in commercial layers

| | | No. of chickens with SG re-isolation from organs (%)[A] | | | | | | | | |
|---|---|---|---|---|---|---|---|---|---|---|
| | No. of | 7 dpc[B] | | | 14 dpc | | | 21 dpc | | |
| Group | chickens | Liver | Spleen | Cecum | Liver | Spleen | Cecum | Liver | Spleen | Cecum |
| Phage-treated | | | | | | | | | | |
| Challenged | 15 | 5/5 (100) | 2/5 (40) | 0/5 (0) | 3/5 (60) | 3/5 (60) | 0/5 (0) | 0/5 (0) | 3/5 (60) | 0/5 (0) |
| Contact | 15 | 0/5 (0) | 0/5 (0) | 0/5 (0) | 0/5 (0) | 0/5 (0) | 0/5 (0) | 1/5 (20) | 1/5 (20) | 0/5 (0) |
| Untreated | | | | | | | | | | |
| Challenged | 15 | 4/5 (80) | 4/5 (80) | 0/5 (0) | 4/5 (80) | 3/5 (60) | 1/5 (20) | 0/5 (0) | 1/5 (20) | 1/5 (20) |
| Contact | 15 | 0/5 (0) | 0/5 (0) | 0/5 (0) | 2/5 (40) | 2/5 (40) | 0/5 (0) | 3/5 (60) | 2/5 (40) | 1/5 (20) |
| Negative control | 15 | 0/5 (0) | 0/5 (0) | 0/5 (0) | 0/5 (0) | 0/5 (0) | 0/5 (0) | 0/5 (0) | 0/5 (0) | 0/5 (0) |

TABLE 11

Effect of ΦCJ2 on mortality caused by horizontal transmission of SG in commercial layers

| | Number of | Antibodies against SG[A] | | Mortality[B] |
|---|---|---|---|---|
| Group | chickens | Pre-challenge | Post-challenge | (%) |
| Phage-treated | | | | |
| SG challenged | 20 | 0/15 | 15/15 | 8/20 (40) |
| SG free | 20 | 0/15 | 15/15 | 1/20 (5)* |
| Untreated | | | | |
| SG challenged | 20 | 0/15 | 15/15 | 11/20 (55) |
| SG free | 20 | 0/15 | 15/15 | 9/20 (45) |
| Negative control | 20 | 0/15 | 0/15 | 0/20 (0) |

[A]RSA tests were performed for SG antibody detection at 2 weeks after challenge; number of chickens positive/number of chickens tested.
[B]Mortality was observed for 3 weeks after challenge; number of chickens positive/number of chickens tested.
*P < 0.05 by Fisher's exact test' as compared to untreated contact chickens In addition, the untreated contact group showed a 40-60% re-isolation rate of the challenge strain in the liver and spleen, while the re-isolation rate in ΦCJ2-treated contact chickens was 20-40% at 3 week post-challenge. Although there were no significant differences in the re-isolation rate of the challenge strain between ΦCJ2-treated and untreated contact chickens, ΦCJ2 treatment reduced the number of chickens colonized with the pathogen after challenge.

INDUSTRIAL APPLICABILITY

The bacteriophage of the present invention has a specific bactericidal activity against *Salmonella typhimurium, Salmonella gallinarum* and *Salmonella Pullorum* without affecting beneficial bacteria, and excellent acid-, heat- and dry-resistance, and thus can be applied to the compositions that can be used for the prevention or treatment of infectious diseases caused by *Salmonella typhimurium, Salmonella gallinarum* and *Salmonella pullorum*, in particular, salmonellosis, *Salmonella* food poisoning, Fowl typhoid, and Pullorum disease, and applied to therapeutics, antibiotics, animal feed, drinking water for animal, sanitizers, and cleaners.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claims is:

1. A method for preventing infectious diseases caused by one or more pathogens selected from the group consisting of *Salmonella typhimurium, Salmonella gallinarum* and *Salmonella pullorum*, which comprises administering an isolated bacteriophage, which is deposited under accession number KCCM10976P, to a subject in need thereof.

2. The method according to claim 1, wherein the infectious disease caused by *Salmonella typhimurium* is salmonellosis or *Salmonella* food poisoning, the infectious disease caused by *Salmonella gallinarum* is Fowl typhoid, and the infectious disease caused by *Salmonella pullorum* is Pullorum disease.

* * * * *